(12) United States Patent
Tamura et al.

(10) Patent No.: US 10,273,569 B2
(45) Date of Patent: Apr. 30, 2019

(54) METAL MASK SUBSTRATE, METAL MASK SUBSTRATE CONTROL METHOD, METAL MASK, AND METAL MASK PRODUCTION METHOD

(71) Applicant: TOPPAN PRINTING CO., LTD., Tokyo (JP)

(72) Inventors: Sumika Tamura, Tokyo (JP); Naoko Mikami, Tokyo (JP); Daisei Fujito, Tokyo (JP); Kiyoaki Nishitsuji, Tokyo (JP); Takehiro Nishi, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 0 days.

(21) Appl. No.: 15/786,463

(22) Filed: Oct. 17, 2017

(65) Prior Publication Data

US 2018/0066352 A1   Mar. 8, 2018

Related U.S. Application Data

(63) Continuation of application No. PCT/JP2016/059042, filed on Mar. 22, 2016.

(30) Foreign Application Priority Data

Jul. 17, 2015 (JP) ................................ 2015-143509
Aug. 31, 2015 (JP) ................................ 2015-171440

(51) Int. Cl.
*H01L 51/00* (2006.01)
*H01L 51/50* (2006.01)
(Continued)

(52) U.S. Cl.
CPC .......... *C23C 14/042* (2013.01); *C23C 14/024* (2013.01); *C23C 14/028* (2013.01);
(Continued)

(58) Field of Classification Search
CPC .. D06M 15/657; D06M 23/08; D06M 15/526; D06M 2200/10; D06M 2101/32;
(Continued)

(56) References Cited

U.S. PATENT DOCUMENTS 6,620,554 B1   9/2003   Komatsu et al.
2003/0221613 A1   12/2003   Kang et al.
(Continued)

FOREIGN PATENT DOCUMENTS

CN   103205680 A   7/2013
JP   H04-314535 A   11/1992
(Continued)

OTHER PUBLICATIONS

Notice of Reasons for Rejection dated Jan. 16, 2018, in Japanese Patent Application No. 2017-529473, 11 pages.
(Continued)

*Primary Examiner* — Nathan L Van Sell
(74) *Attorney, Agent, or Firm* — Squire Patton Boggs (US) LLP

(57) ABSTRACT

A metal mask substrate includes a metal surface to which a resist is to be disposed. A specular reflectance of incident light to the surface is 45.2% or more.

6 Claims, 9 Drawing Sheets

(51) Int. Cl.

| | | |
|---|---|---|
| H01L 51/52 | (2006.01) | |
| C23C 14/02 | (2006.01) | |
| C23C 14/04 | (2006.01) | |
| C23C 14/08 | (2006.01) | |
| C23C 14/12 | (2006.01) | |
| C23C 14/22 | (2006.01) | |
| C23F 1/02 | (2006.01) | |
| C23F 1/44 | (2006.01) | |
| G01N 21/55 | (2014.01) | |
| G03F 7/00 | (2006.01) | |
| C23F 1/14 | (2006.01) | |

(52) U.S. Cl.
CPC ............ *C23C 14/085* (2013.01); *C23C 14/12* (2013.01); *C23C 14/225* (2013.01); *C23F 1/02* (2013.01); *C23F 1/14* (2013.01); *C23F 1/44* (2013.01); *G01N 21/55* (2013.01); *G03F 7/0002* (2013.01); *H01L 51/5012* (2013.01); *H01L 51/5271* (2013.01); *H01L 51/0011* (2013.01)

(58) Field of Classification Search
CPC ....... D06M 2200/12; C09D 7/67; C09D 5/00; C09D 7/68; C09D 183/08; C09D 127/12; C23C 14/042; C23C 14/12; C23C 14/028; C23C 14/085; C23C 14/225; G03F 7/0002; C23F 1/02; C23F 1/14; C23F 1/44; G01N 21/55; H01L 51/5271; H01L 51/5012; H01L 51/0011
See application file for complete search history.

(56) References Cited

U.S. PATENT DOCUMENTS

| | | | |
|---|---|---|---|
| 2004/0018372 A1 | 1/2004 | Komatsu et al. | |
| 2004/0175633 A1* | 9/2004 | Shoki | B82Y 10/00 430/5 |
| 2004/0224526 A1* | 11/2004 | Shoki | B82Y 10/00 430/5 |
| 2008/0277157 A1* | 11/2008 | Naito | H01F 41/34 174/392 |
| 2013/0263749 A1 | 10/2013 | Kernig et al. | |
| 2014/0377903 A1 | 12/2014 | Takeda et al. | |
| 2016/0049586 A1 | 2/2016 | Takeda et al. | |
| 2016/0208392 A1 | 7/2016 | Ikenaga et al. | |
| 2016/0268511 A1 | 9/2016 | Takeda et al. | |
| 2016/0293844 A1 | 10/2016 | Takeda et al. | |
| 2017/0141315 A1 | 5/2017 | Ikenaga | |
| 2017/0186955 A1 | 6/2017 | Takeda et al. | |

FOREIGN PATENT DOCUMENTS

| | | |
|---|---|---|
| JP | H09-209176 A | 8/1997 |
| JP | H11-140667 A | 5/1999 |
| JP | 2002-151841 A | 5/2002 |
| JP | 2002-246712 A | 8/2002 |
| JP | 2004-276435 A | 10/2004 |
| JP | 2005-76068 A | 3/2005 |
| JP | 2006-233285 A | 9/2006 |
| JP | 2008-41553 A | 2/2008 |
| JP | 2009-127105 A | 6/2009 |
| JP | 2010-214447 A | 9/2010 |
| JP | 2011-166018 A | 8/2011 |
| JP | 2013-209710 A | 10/2013 |
| JP | 2013-542327 A | 11/2013 |
| JP | 2013-245392 A | 12/2013 |
| JP | 2014-208910 A | 11/2014 |
| JP | 5641462 B1 | 11/2014 |
| JP | 2015-055007 A | 3/2015 |
| JP | 2015-117432 A | 6/2015 |
| JP | 2015-129333 A | 7/2015 |
| JP | 2015-129334 A | 7/2015 |
| KR | 2003-0092790 A | 12/2003 |
| WO | WO 2013/105643 A1 | 7/2013 |
| WO | WO 2014/038510 A1 | 3/2014 |

OTHER PUBLICATIONS

International Preliminary Report on Patentability dated Jan. 23, 2018, in International Patent Application No. PCT/JP2016/059042, 12 pages.
Japanese Standards Association, *Definitions and Designation of Surface Roughness*, JIS B 0601: 1982, 20 pages.
Japanese Standards Association, *Geometrical Product Specifications (GPS)—Surface texture: Profile method—Terms, definitions and surface texture parameters*, JIS B 0601: 2001, 31 pages.
International Organization for Standardization, *Geometrical product specifications (GPS)—Surface texture: Areal*, ISO 25178-2:2012(E), pp. iv and 9.
Office Action dated Feb. 26, 2018, in Taiwanese Patent Application No. 10720169960, 6 pages.
Office Action dated Mar. 2, 2018, in Chinese Patent Application No. 201680012997.X, 11 pages.
Office Action dated Mar. 15, 2018, in Chinese Patent Application No. 201680013003.6, 7 pages.
Notification of Reasons for Refusal dated May 7, 2018, in Japanese Patent Application No. 2017-529473, 5 pages.

\* cited by examiner

METAL MASK SUBSTRATE, METAL MASK SUBSTRATE CONTROL METHOD, METAL MASK, AND METAL MASK PRODUCTION METHOD

BACKGROUND

The present disclosure relates to a metal mask substrate having a metal surface for resist deposition such as a metal mask substrate for use in forming a metal mask for organic EL devices, a method for controlling a metal mask substrate, a metal mask, and a method for manufacturing a metal mask.

In manufacturing of metal masks for organic EL devices, metal mask substrates in the form of a metal plate are used. A coating liquid containing materials to form a resist layer is applied to the surface to be coated of a metal mask substrate to thereby form a resist layer. The resist layer is subjected to exposure and development, so that a resist layer having a specified pattern is formed. The metal mask substrate is etched through the resist layer to thereby produce a metal mask.

In forming of the resist layer described above, the thickness of a resist layer or the in-plane thickness of a resist layer may vary in some cases, due to the variation in the amount of coating liquid to be applied to the surface to be coated or the variation in extent of drying of the coating liquid. In order to suppress such variations in a resist layer, use of a dry film resist as a resist layer has been proposed (for example, refer to Japanese Laid-Open Patent Publication No. 2013-209710).

A resist layer formed from coating liquid is a cured layer of the coating liquid applied directly to the surface of a metal mask substrate, so that a shape tracing the surface to be coated can be easily formed, and thus, the resist layer formed from coating liquid is easy to adhere to the metal mask substrate without difficulty. On the other hand, a resist layer formed from dry film resist is a layer independent layer from the metal mask substrate and adhering to a metal mask substrate surface. Therefore, the resist layer formed from dry film resist has a shape more difficult to follow the surface to be coated in comparison with a resist layer formed from coating liquid, so that a part of the resist layer may be detached from the metal mask substrate in some cases.

The above described the same circumstances apply not only to metal mask substrates formed from metal plate but also to metal mask substrates having a metal or alloy surface in contact with a resist layer such as a laminate of a resin layer and a metal layer or a laminate having metal layers and a resin layer sandwiched therebetween. Even in the case of a resist layer formed from coating liquid containing materials to form a resist layer, the resist layer is under the same circumstances, as far as having low adhesion to a metal mask substrate.

SUMMARY

An objective of the present disclosure is to provide a metal mask substrate, a method for controlling metal mask substrates, a metal mask, and a method for manufacturing metal masks that have a surface that provides enhanced adhesion at the interface between a resist and the surface.

To achieve the foregoing objective and in accordance with one aspect of the present disclosure, a metal mask substrate is provided that includes a metal surface to which a resist is to be disposed. A specular reflectance of incident light to the surface is 45.2% or more.

To achieve the foregoing objective and in accordance with one aspect of the present disclosure, a method for controlling metal mask substrates is provided. The method includes: preparing a metal mask substrate having a metal surface to which a resist is to be disposed; providing incident light to the surface; measuring an intensity of a specular reflected light from the incident light to the surface; calculating, as a specular reflectance, a ratio of the intensity of specular reflected light to the intensity of the incident light to the surface; and determining whether or not the specular reflectance is 45.2% or more.

Through extensive investigation of the surface state of metal mask substrates, the present inventors have found that the specular reflectance of the incident light to the surface has the following correlation with each of the three-dimensional surface roughness $Sa$ of the surface and the three-dimensional surface roughness $Sz$ of the surface. In other words, it has been found that as each of the three-dimensional surface roughness $Sa$ and the three-dimensional surface roughness $Sz$ decreases, the specular reflectance increases.

It has then been found that with a specular reflectance of 45.2% or more, the surface roughness decreases to the extent that a resist cannot be easily detached from the surface due to enhanced adhesion at the interface between the resist and the surface.

In this context, with the above-described configuration, the specular reflectance of the incident light to the surface is 45.2% or more, so that the adhesion at the interface between the surface of a metal mask substrate and a resist can be enhanced.

In the above-described metal mask substrate, the metal mask substrate has a width direction orthogonal to a rolling direction of the metal mask substrate, and a specular reflectance in a first plane orthogonal to the surface and orthogonal to the rolling direction is a first reflectance. A specular reflectance in a second plane orthogonal to the surface and orthogonal to the width direction is a second reflectance. The second reflectance is larger than the first reflectance, and the first reflectance is 45.2% or more.

With the above-described configuration, the relatively small reflectance of the two reflectances obtained at the surface is 45.2% or more. Thus, the adhesion at the interface between the surface of a metal mask substrate and a resist is further enhanced.

In the above-described metal mask substrate, the surface may include a portion in which a difference obtained by subtracting the first reflectance from the second reflectance is 10.2% or more.

With the above-described configuration, the surface includes a portion where the second reflectance is larger than the first reflectance by 10.2% or more, which is preferred to further enhance the adhesion at the interface between the surface of a metal mask substrate and a resist.

In the above-described metal mask substrate, the surface may have a three-dimensional surface roughness $Sa$ of 0.11 μm or less and a three-dimensional surface roughness $Sz$ of 3.17 μm or less.

With the above-described configuration, with a specular reflectance at the surface of a metal mask substrate of 45.2% or more, the three-dimensional surface roughness $Sa$ is 0.11 μm or less and the three-dimensional surface roughness $Sz$ is 3.17 μm or less. Thus, the adhesion at the interface between a resist and the surface is more reliably enhanced.

In the above-described metal mask substrate, the surface is a first surface, and the resist is a first resist. The metal mask substrate further includes a metal second surface to which a resist is to be disposed. The second surface is a surface opposite to the first surface. A specular reflectance of incident light to the second surface may be 45.2% or more.

With the above-described configuration, the adhesion between the first surface and the first resist and the adhesion between the second surface and the second resist is enhanced. Thus, the processing accuracy is improved in etching of the first and second surfaces.

In the above-described metal mask substrate, the surface may be made of invar.

With the above-described configuration, the linear expansion coefficient of a glass substrate is almost equivalent to the linear expansion coefficient of invar. Thus, a metal mask formed from the metal mask substrate can be applied to film formation on a glass substrate. In other words, a metal mask having improved shape accuracy can be applied to film formation on a glass substrate.

In the above-described metal mask substrate, the resist is a dry film resist. The dry film resist is preferably adhered to the surface.

In the above-described method for controlling metal mask substrates, the resist is a dry film resist. The dry film resist is preferably adhered to the surface.

With the above-described configuration, the adhesion between the metal surface to be adhered to a dry film resist and the dry film resist is enhanced.

To achieve the foregoing objective and in accordance with one aspect of the present disclosure, a metal mask is provided that includes a metal mask substrate having a metal surface. The metal mask substrate has a plurality of through-holes extending through the metal mask substrate in a thickness direction of the metal mask substrate. The through-holes each have an opening in the surface. The value represented by (B/A)×100(%) is 10% or less, where A represents an average dimension of the openings in a plan view facing the surface, and B represents a value obtained by multiplying a standard deviation of the dimension by three.

To achieve the foregoing objective and in accordance with one aspect of the present disclosure, a method for manufacturing metal masks is provided. The method includes: preparing a metal mask substrate having a metal surface to which a resist is to be disposed, the surface having a three-dimensional surface roughness Sa of 0.11 µm or less and a three-dimensional surface roughness Sz of 3.17 µm or less; disposing a resist on the surface; forming through-holes in the resist, the through-holes being for forming a plurality of cavities in the metal mask substrate, each cavity extending in the thickness direction of the metal mask substrate and having an opening in the surface; and forming a plurality cavities in the metal mask substrate through the resist, such that (B/A)×100(%) is 10% or less, where A represents an average dimension of the openings in a plan view facing the surface, and B represents a value obtained by multiplying a standard deviation of the dimension by three.

With the above-described configuration, (B/A)×100(%) is 10% or less. Thus, the dimensional accuracy at the opening is high.

DESCRIPTION OF EXEMPLARY EMBODIMENTS

With reference to FIGS. 1 to 22, there will be described below one embodiment of a metal mask substrate and a method for controlling metal mask substrates of the present-disclosure as a metal mask substrate for dry film resist and a method for controlling metal mask substrates for dry film resist, and one embodiment of a metal mask and a method for manufacturing metal masks. The metal mask manufactured using the metal mask substrate for dry film resist in the present embodiment is a metal mask for use in vapor-depositing an organic material to constitute an organic EL device on a glass substrate in the manufacturing process of an organic EL device. The structure of a metal mask substrate for dry film resist, the method for controlling metal mask substrates for dry film resist, the method for manufacturing metal mask substrates for dry film resist, the method for manufacturing metal masks, and Examples will be described one by one below.

<Structure of Metal Mask Substrate for Dry Film Resist>

With reference to FIGS. 1 to 4, a structure of metal mask substrates for dry film resist will be described below.

Figure 1:
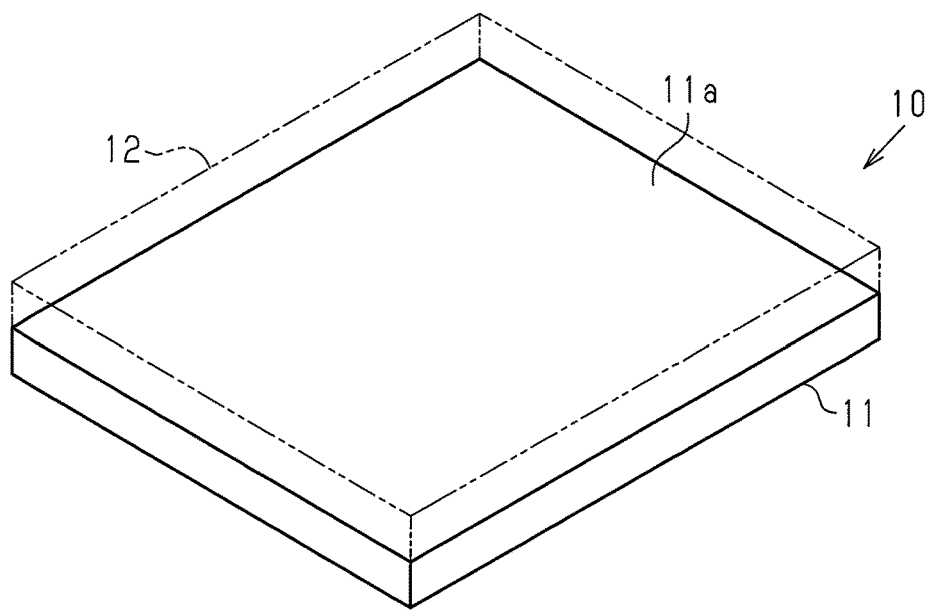
FIG. 1 is a partial perspective view showing a partial perspective structure of a metal mask substrate for dry film resist in an embodiment of the metal mask substrate of the present disclosure as metal mask substrate for dry film resist.

As shown in FIG. 1, a metal mask substrate 11 is a metal mask substrate for dry film resist as an example, which is a metal layer spreading along one surface. The metal mask substrate 11 includes a first surface 11a of metal, which is a surface as an example on which a resist is disposed, more specifically a surface as an example to which a dry film resist is adhered. At the first surface 11a, the specular reflectance of incident light to the first surface 11a is 45.2% or more.

The specular reflectance is the reflectance in specular reflection of light emitted from a halogen lamp having an incident angle of 45°±0.2° to the normal direction of the first surface 11a of the metal mask substrate 11. The reflectance is a value calculated from the following expression (1).

Reflectance (%)={(Intensity of light in specular reflection)/(Intensity of incident light)}×100   (1)

Such a metal mask substrate 11 has a specular reflectance of the incident light to the first surface 11a of 45.2% or more. This enhances the adhesion at the interface between the first surface 11a of the metal mask substrate 11 and a first dry film resist 12 as an example of the dry film resist adhered to the surface.

The laminate including the metal mask substrate 11 having a first surface 11a to which a first dry film resist 12 is an intermediate 10 to form a metal mask, which is used as an intermediate to form a metal mask.

The rolling direction of the metal mask substrate 11 is the rolling direction in manufacturing of the metal mask substrate 11, and the width direction is the direction orthogonal to the rolling direction.

Among the reflectances, at the first surface 11a of the metal mask substrate 11, a first reflectance is the specular reflectance in a first plane orthogonal to the first surface 11a and the rolling direction. A second reflectance is the specular reflectance in a second plane orthogonal to the first surface 11a and the width direction. At the first surface 11a, the second reflectance is larger than the first reflectance, with the first reflectance being 45.2% or more.

The relatively small reflectance of the two reflectances obtained at the first surface 11a is 45.2% or more. This further enhances the adhesion at the interface between the surface of the metal mask substrate 11 and the dry film resist 12.

The first surface 11a includes a portion where the difference obtained by subtracting the first reflectance from the second reflectance is 10.2% or more. The first surface 11a includes the portion where the second reflectance is larger than the first reflectance by 10.2% or more, which is more preferred to enhance the adhesion at the interface between the first surface 11a of the metal mask substrate 11 and the dry film resist 12.

The first surface 11a has a three-dimensional surface roughness Sa of 0.11 µm or less and a three-dimensional surface roughness Sz of 3.17 µm or less.

The three-dimensional surface roughness Sa and the three-dimensional surface roughness Sz are the values measured by a method in accordance with ISO 25178. The three-dimensional surface roughness Sa is the arithmetic mean height Sa in a defined region having a specified area, and the three-dimensional surface roughness Sz is the maximum height Sz in a defined region having a specified area.

The metal mask substrate 11 has a three-dimensional surface roughness Sa of 0.11 µm or less and a three-dimensional surface roughness Sz of 3.17 µm or less, with a specular reflectance of 45.2% or more, so that the adhesion at the interface between the first dry film resist 12 and the first surface 11a is more reliably enhanced.

A preferred material to form the metal layer is, for example, invar, i.e. an alloy mainly composed of iron and nickel with a nickel content of 36 mass %. In other words, the surface of the metal mask substrate 11 is preferably made of invar. The linear expansion coefficient of invar is about $1.2 \times 10^{-6}/°C$. Preferably the metal layer has a thickness of, for example, 10 µm or more and 50 µm or less.

Since the linear expansion coefficient of a glass substrate is almost equivalent to the linear expansion coefficient of invar, a metal layer formed of invar allows a metal mask formed from the metal mask substrate 11 to be applied to film formation on a glass substrate. In other words, a metal mask having improved shape accuracy can be applied to film formation on a glass substrate.

The first dry film resist 12 is formed of, for example, a negative resist as an example of materials having photosensitivity. The material to form the first dry film resist 12 is, for example, an acrylic resin that is cross-linkable by photopolymerization. Preferably the first dry film resist 12 has a thickness of, for example, 5 µm or more and 20 µm or less. Although the first dry film resist 12 may be formed of positive resist, a negative resist is generally used as the material to form the first dry film resist 12 in many cases.

Figure 2:
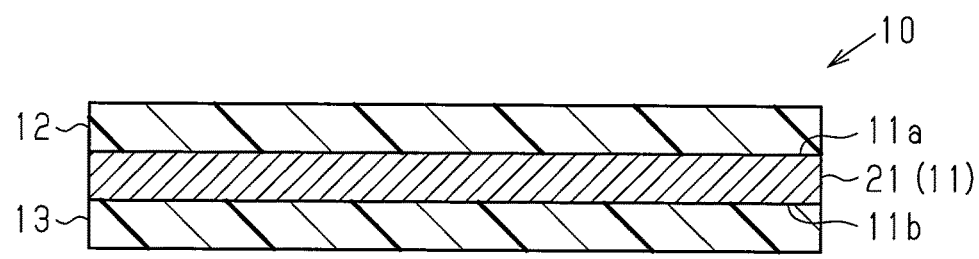
FIG. 2 is a partial cross-sectional view showing a partial cross-sectional structure of a metal mask substrate for dry film resist as an example.
Figure 3:
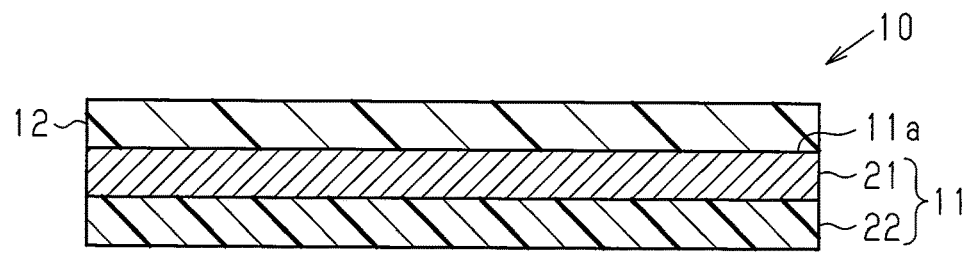
FIG. 3 is a partial cross-sectional view showing a partial cross-sectional structure of a metal mask substrate for dry film resist as an example.
Figure 4:
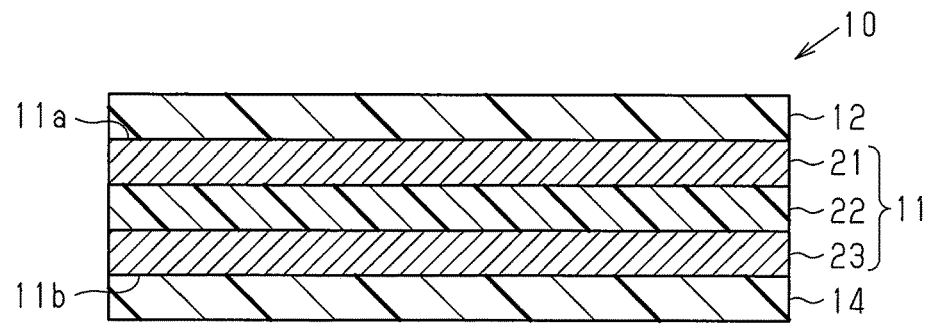
FIG. 4 is a partial cross-sectional view showing a partial cross-sectional structure of a metal mask substrate for dry film resist as an example.

With reference to FIGS. 2 to 4, other modes of the metal mask substrate 11 and the intermediate 10 to form a metal mask will be described below. In FIG. 2, a first mode is shown as an example of the metal mask substrate 11 comprising one metal layer. In FIG. 3, a second mode is shown as an example of the metal mask substrate 11 comprising one metal layer and one resin layer. In FIG. 4, a third mode is shown as an example of the metal mask substrate 11 comprising two metal layers and one resin layer.

<First Mode>

As shown in FIG. 2, a metal layer 21 has a second surface 11b on the opposite side to a first surface 11a. The first surface 11a is a metal surface to which a first dry film resist 12 is to be adhered. The second surface 11b is a metal surface to which a resist is to be disposed, or more specifically, a second dry film resist 13 is to be adhered. An intermediate 10 to form a metal mask comprises the metal layer 21, the first dry film resist 12, and the second dry film resist 13.

Preferably the second surface 11b also has a specular reflectance of 45.2% or more as with the first surface 11a. The metal mask substrate 11 allows the adhesion between the second dry film resist 13 and the metal layer 21 to be enhanced at the second surface 11b also, in addition to the first surface 11a of the metal layer 21.

Preferably the second surface 11b also has a three-dimensional surface roughness Sa of 0.11 μm or less and a three-dimensional surface roughness Sz of 3.17 μm or less as with the first surface 11a. Such a metal mask substrate 11 allows the adhesion at the interface between the second dry film resist 13 and the second surface 11b to be more reliably enhanced at the second surface 11b also, in addition to the first surface 11a of the metal layer 21.

The material to form the second dry film resist 13 is, for example, an acrylic resin which is cross-linkable by photopolymerization as with the first dry film resist 12. Preferably the second dry film resist 13 has a thickness of, for example, 5 μm or more and 20 μm or less.

<Second Mode>

As shown in FIG. 3, a metal mask substrate 11 may comprise a metal layer 21 and a resin layer 22 located opposite to the first dry film resist 12 across the metal layer 21. Preferably the linear expansion coefficient of the resin layer 22 and the linear expansion coefficient of the metal layer 21 tend to develop the same temperature dependency, respectively, having comparable values. The metal layer 21 is, for example, an invar layer made of invar, and the resin layer 22 is, for example, a polyimide layer made of polyimide. The metal mask substrate 11 prevents warping caused by the difference between the linear expansion coefficient of the metal layer 21 and the linear expansion coefficient of the resin layer 22.

An intermediate 10 to form a metal mask in the second mode comprises a metal layer 21, a first dry film resist 12, and a resin layer 22. The resin layer 22 may be formed by coating on the metal layer 21, or may be a film adhered to the metal layer 21, in which the film is formed separately from the metal layer 21. The resin layer 22 may include an adhesive layer exhibiting adhesion to the metal layer 21, the adhesive layer being adhered to the metal layer 21.

<Third Mode>

As shown in FIG. 4, in addition to a metal layer 21 and a resin layer 22, a metal mask substrate 11 may further comprise another metal layer 23 located opposite to the metal layer 21 across the resin layer 22 in the thickness direction of the metal mask substrate 11. In the metal mask substrate 11, the metal layer 23 includes a second surface 11b on the opposite side to the first surface 11a of the metal mask substrate 11.

A preferred material to form the other metal layer 23 is, for example, invar, i.e. an alloy mainly composed of iron and nickel with a nickel content of 36 mass %, as with the metal layer 21. Preferably the metal layer 23 has a thickness of, for example, 10 μm or more and 50 μm or less. The thickness of the other metal layer 23 and the thickness of the metal layer 21 may be the same or different from each other.

As with the first surface 11a and the second surface 11b included in the metal layer 21, preferably the second surface 11b included in the other metal layer 23 has a specular reflectance of 45.2% or more. Also, preferably the second surface 11b included in the other metal layer 23 has a three-dimensional surface roughness Sa of 0.11 μm or less and a three-dimensional surface roughness Sz of 3.17 μm or less.

Such a second surface 11b of the other metal layer 23 has advantages equivalent to those of the first surface 11a and the second surface 11b included in the metal layer 21. The metal mask substrate 11 has a structure including a laminate of the metal layer 21 and the resin layer 22 and a laminate of the metal layer 23 and the resin layer 22, so that advantages equivalent to those of the metal mask substrate 11 described with reference to FIG. 3, i.e. the metal mask substrate 11 in the second mode, are achieved.

An intermediate 10 to form a metal mask in the third mode comprises metal layers 21 and 23, a first dry film resist 12, a resin layer 22 and a second dry film resist 14. The resin layer 22 may be formed by coating on any of the two metal layers 21 and 23, or may be a film adhered to the metal layers 21 and 23, in which the film is formed separately from the metal layers 21 and 23. In the case of a resin layer 22 to be adhered to the metal layers 21 and 23, the resin layer 22 may include an adhesive layer exhibiting adhesion to the metal layer 21 and an adhesive layer exhibiting adhesion to the metal layer 23, the adhesive layers being adhered to the two metal layers 21 and 23, respectively.

<Method for Controlling Metal Mask Substrate for Dry Film Resist>

Figure 5:
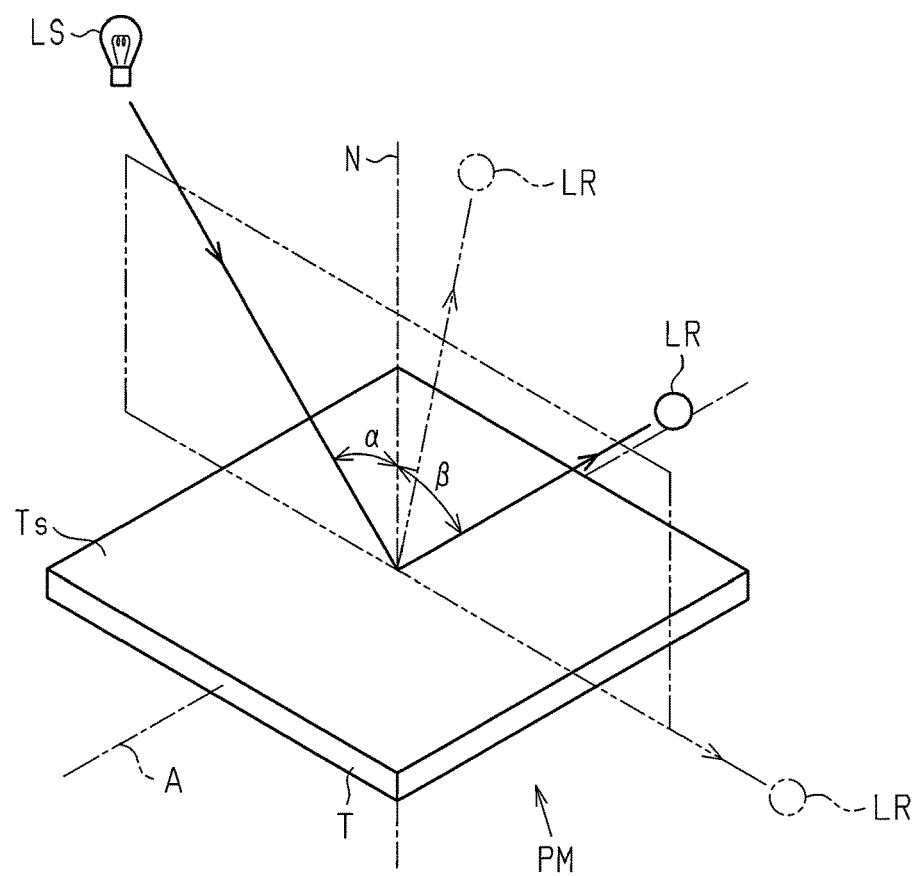
FIG. 5 is a process drawing illustrating a method for controlling metal mask substrates for dry film resist in an embodiment of the method for controlling metal mask substrates of the present disclosure as the method for controlling metal mask substrate for dry film resist.

With reference to FIG. 5, a method for controlling metal mask substrates for dry film resist will be described below.

The method for controlling metal mask substrates for dry film resist comprises a preparation step, a step of providing incident light, a measurement step, a calculation step, and a determination step. In other words, the method for controlling metal mask substrates for dry film resist comprises preparing a metal mask substrate for dry film resist having a metal surface to which a dry film resist is to be adhered, and providing incident light to the surface of the metal mask substrate for dry film resist. The method for controlling metal mask substrates for dry film resist further comprises measuring the intensity of the specular reflected light from the surface exposed to the incident light, calculating the specular reflectance as the ratio of the intensity of specular reflected light to the intensity of incident light, and determining whether or not the reflectance is 45.2% or more.

As shown in FIG. 5, in the step of providing incident light and the measurement step described above, for example, an automated goniophotometer PM is used. The automated goniophotometer PM comprises a light source LS, i.e. a halogen lamp, and a light receiver LR, which receives light reflected from a test piece disposed in the automated goniophotometer PM.

Prior to the step of providing incident light, a part of the metal mask substrate for dry film resist is cut out to prepare a test piece T. The test piece T has a measurement surface Ts, which is a part of the surface of the metal mask substrate for dry film resist. The test piece T is disposed in the automated goniophotometer PM, such that the measurement surface Ts is exposed to the incident light from the light source LS.

The angle formed between the normal direction N of the measurement surface Ts of a test piece T and the incident direction of light emitted from a light source LS is defined as incident angle α of light emitted from the light source LS. In the step of providing incident light, the measurement surface Ts receives incident light at a specified incident angle α, for example, at an incident angle α of 45°±0.2°. The intensity of incident light to the measurement surface Ts is the intensity of light emitted from the light source LS.

The angle formed between the normal direction N of the measurement surface Ts and the direction of light emitted from measurement surface Ts is defined as emitting angle β of light emitted from the measurement surface Ts. The emitting angle β of light specular reflected from the measurement surface Ts is equal to the incident angle α of incident light to the measurement surface Ts. In other words, the emitting angle β of specular reflected light is 45°±0.2°.

In the measurement step, a light receiving device included in the light receiver LR receives at least specular reflected light in the light reflected light from the measurement surface Ts. The light receiving device included in the light receiver LR creates analog signals corresponding to the intensity of the received light, and a conversion circuit included in the light receiver LR converts the analog signals created by the light receiving device to digital signals so as to create the digital signals as the intensity of the reflected light.

The light receiving device included in the light receiver LR receives light having an emitting angle β in the range, for example, from 0° to 90° at intervals of 0.1°. On this occasion, the light receiving device included in the light receiver LR rotates around the rotation axis A extending orthogonally to the normal direction N, along the measurement surface Ts of a test piece T. In other words, the test piece T is disposed such that the rotation axis A around which the light receiving device rotates runs in parallel with the measurement surface Ts. Of light reflected from the measurement surface Ts, light having an emitting angle β in the range from 0° to 90° is thereby subjected to the measurement of light intensity at intervals of 0.1°, in the measurement step.

The calculation step is performed, for example, by an arithmetic part included in the light receiver LR built in an automated goniophotometer PM based on the signal current photoelectrically converted from the intensity of light received by the light receiver LR. The determination step is performed by an arithmetic unit connected to the automated goniophotometer PM. The arithmetic part calculates the reflectance of light for each emitting angle β, for example, by substituting the pre-inputted intensity of incident light and the intensity of the reflected light, i.e. the digital signals created in the measurement step, into the expression (1) described above. The automated goniophotometer PM outputs the calculated reflectance of light as digital signals to the arithmetic unit.

The arithmetic unit then determines whether or not the specular reflectance is 45.2% or more based on the digital signals outputted from the automated goniophotometer PM. According to the control method, it is determined whether or not the specular reflectance is 45.2% or more at the surface of a metal mask substrate, so that the metal mask substrate for dry film resist can be controlled to have the surface in a state for enhancing adhesion at the interface between the dry film resist and the surface.

The surface state of a metal mask substrate for dry film resist is generally controlled based on the surface roughness in many cases. The region of which the surface roughness can be measured at one time is, for example, a very small rectangular region having a side length of about several hundred μm. In order to accurately understand the almost entire surface state of a metal mask substrate for dry film resist based on the measurement values of the surface roughness, it is therefore required to measure the surface roughness at a great many places of a metal mask substrate for dry film resist.

In contrast, the region where the specular reflectance can be measured at one time is significantly larger than the region where the surface roughness can be measured at one time, and the time required to obtain the reflectance is significantly shorter than the time required to obtain the surface roughness. In the control to ensure the adhesion between the surface of a metal mask substrate for dry film resist and a dry film resist, a control to macroscopically comprehend the surface state is preferred in comparison with the measurement of the surface roughness described above. In that respect, the size of the region where the specular reflectance can be measured at one time is easily enlarged to the range having an effect on the adhesion between the surface of a metal mask substrate for dry film resist and a dry film resist. In contrast to a one surface roughness value, one reflectance value is, therefore, the value reflecting the surface state in a larger region of a metal mask substrate for dry film resist, and the load required to obtain the value is small.

In contrast to the control of metal mask substrates for dry film resist based on the surface roughness, the control of metal mask substrates for dry film resist based on the reflectance therefore allows the surface state to be accurately comprehended to the same degree, even in dependence on a reduced number of measurement spots on the surface.

In contrast to the control of metal mask substrates for dry film resist based on the surface roughness, the control of metal mask substrates for dry film resist based on the reflectance therefore allows the surface state to be more accurately comprehended in dependence on the same number of measurement spots on the surface.

The control of metal mask substrates for dry film resist based on the surface roughness is performed using two values, i.e. the three-dimensional surface roughness Sa and the three-dimensional surface roughness Sz in some cases. In contrast thereto, the control of metal mask substrates for dry film resist based on the reflectance can be performed based on a measured specular reflectance value only. In other words, since the metal mask substrate for dry film resist can be controlled based on one value, the smaller load is required to control a metal mask substrate for dry film resist in comparison with the control of metal mask substrates for dry film resist based on the surface roughness.

The calculation step may be performed by a device other than the automated goniophotometer PM, using the measurement results obtained from the automated goniophotometer PM, and the determination step may be performed by the automated goniophotometer PM.

<Method for Manufacturing Metal Mask Substrate for Dry Film Resist>

Figure 6:
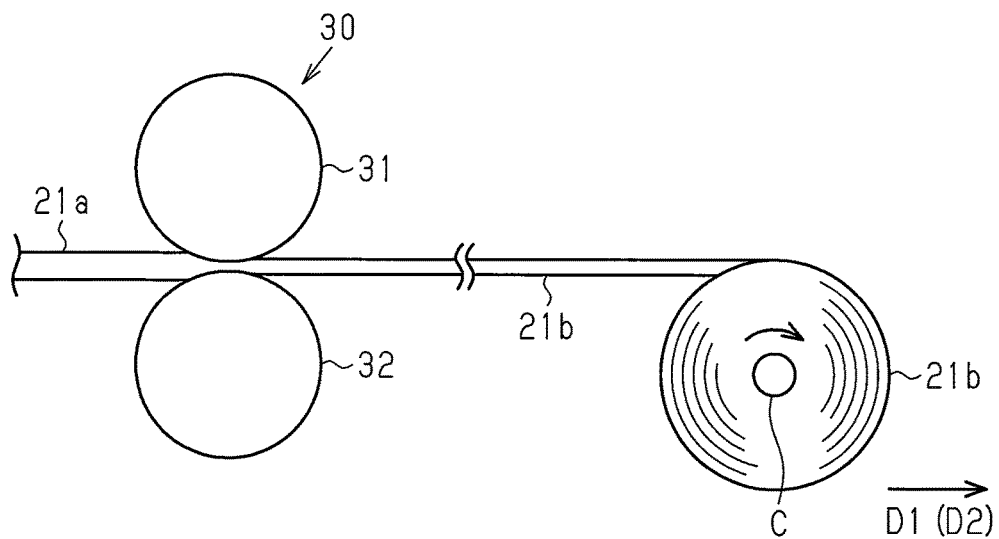
FIG. 6 is a process drawing illustrating a method for manufacturing metal mask substrates for dry film resist, in which a process for rolling a base material formed from invar is shown.
Figure 7:
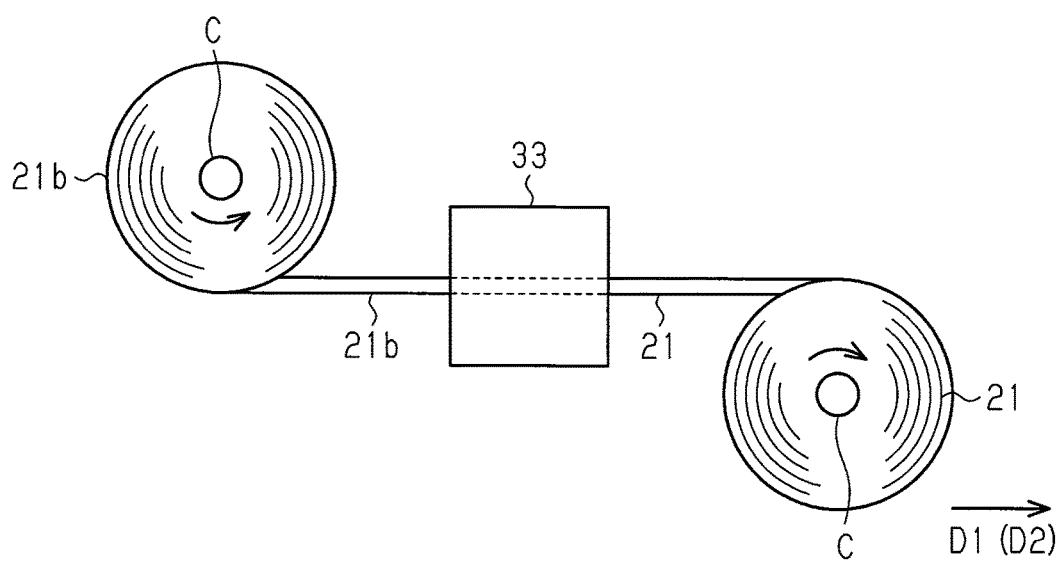
FIG. 7 is a process drawing illustrating a method for manufacturing metal mask substrates for dry film resist, in which a process for annealing a rolled material is shown.

With reference to FIGS. 6 and 7, a method for manufacturing metal mask substrates for dry film resist will be described below.

With reference to FIGS. 6 and 7, a method for manufacturing metal mask substrates for dry film resist will be described below. Hereinafter, a metal mask substrate 11 comprising one metal layer 21, i.e. a first mode described with reference to FIG. 2, will be described as an example.

As shown in FIG. 6, in the method for manufacturing metal mask substrates for dry film resist, first a base material 21a formed of invar extending in one direction, i.e. rolling direction D1, is prepared. Subsequently, the base material 21a is transported in a transporting direction D2 toward a rolling device 30 having a pair of rollers 31 and 32, such that the rolling direction D1 of the base material 21a runs parallel with the transporting direction D2 of the base material 21a.

The base material 21a reaches between a pair of rollers 31 and 32 so as to be rolled by the pair of rollers 31 and 32. The thickness of the base material 21a is thereby reduced, and the base material 21a is stretched along the transporting direction D2, so that a rolled material 21b can be obtained. The rolled material 21b is wound around a core C. The rolled material 21b may be handled in a stretched belt shape without being wound around the core C. The rolled material 21b has a thickness of, for example, 10 μm or more and 50 μm or less.

As shown in FIG. 7, in order to remove the residual stress accumulated inside the rolled material 21b formed by rolling the base material 21a, the rolled material 21b is annealed with an annealing device 33. A metal layer 21 as metal mask substrate is thereby obtained. Since the rolled material 21*b* is annealed during stretching of the rolled material 21*b* in the transporting direction D2, the metal layer 21 as metal mask substrate having lower residual stress can be obtained than the rolled material 21*b* before annealing.

Each of the rolling step and the annealing step described above may be performed with the following modifications. For example, in the rolling step, a rolling device having a plurality of pairs of rollers may be used. The rolling step and the annealing step may be repeated several times in manufacturing of the metal layer 21. In the annealing step, the rolled material 21*b* may be annealed in a wound state around the core C, instead of annealing the rolled material 21*b* during stretching the rolled material 21*b* in the transporting direction D2.

In the case of annealing step of the rolled material 21*b* in a wound state around the core C, the metal layer 21 may tend to warp corresponding to the diameter of the metal layer 21 after annealing in some cases, due to winding of the rolled material 21*b* around the core C. Depending on the diameter size of the metal layer 21 wound around the core C and the material to form the base material 21*a*, it is therefore preferred to anneal the rolled material 21*b* during stretching of the rolled material 21*b* in the transporting direction D2.

<Method for Manufacturing Metal Masks>

With reference to FIGS. 8 to 14, a method for manufacturing metal masks will be described below. Hereinafter, a metal mask substrate 11 for use in manufacturing metal masks comprising one metal layer 21, i.e. the first mode described with reference to FIG. 2, is described as an example. In FIGS. 8 to 13, a process drawing of a portion including one through-hole only is shown for convenience in drawing, though the metal mask has a plurality of through-holes.

A method for manufacturing metal masks comprises the steps of: preparing a metal mask substrate having a metal surface; disposing a resist on the surface; forming a plurality of through-holes in the resist, the through-holes being for forming a plurality of cavities in the metal mask substrate, the cavity extending in the thickness direction of the metal mask substrate and having an opening in the surface; and forming a plurality of cavities in the metal mask substrate. In forming a plurality of cavities in the metal mask substrate, preferably a plurality of cavities are formed in the metal mask substrate such that (B/A)×100(%) is 10% or less, where A represents the average dimension of the openings in the plan view facing the surface, and B represents the value obtained by multiplying the standard deviation of the dimension by three.

In the case where the cavity of a metal mask substrate is a pore defining a circular region in the plan view facing the surface of the metal mask substrate, the dimension of the opening of the cavities may be the diameter of the opening. In the case where the cavity of a metal mask substrate is a pore defining a rectangular region extending in a direction in the plan view facing the surface of the metal mask substrate, the dimension of the opening of the cavities may be the dimension in the longitudinal direction of the opening or the dimension in the transverse direction of the opening. In the case where the cavity of a metal mask substrate is a pore defining a square region in the plan view facing the surface of the metal mask substrate, the dimension of the opening of the cavities may be a side dimension of the opening.

In the case where the cavity is a pore defining a rectangular region extending in a direction or cavities defining a square region, the corners of the region defined by the cavity may have an arc shape with a center of curvature located inside the region defined by the cavity.

Figure 8:
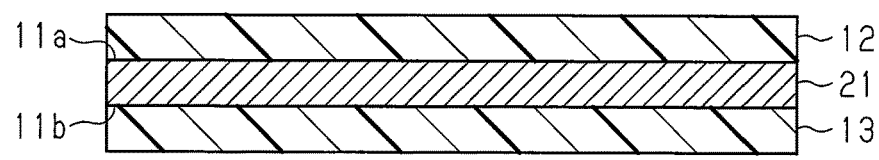
FIG. 8 is a process drawing illustrating a method for manufacturing metal masks, in which a process for sticking a dry film resist is shown.

More specifically, as shown in FIG. 8, in manufacturing a metal mask, first a metal mask substrate, i.e. a metal layer 21 including the first surface 11*a* and the second surface 11*b* described above, a first dry film resist 12 to be adhered to the first surface 11*a*, and a second dry film resist 13 to be adhered to the second surface 11*b* are prepared. Each of the two dry film resists 12 and 13 is a film formed separately from the metal layer 21.

The first dry film resist 12 is adhered to the first surface 11*a*, and the second dry film resist 13 is adhered to the second surface 11*b*. In other words, the first dry film resist 12 is laminated on the first surface 11*a*, and the second dry film resist 13 is laminated on the second surface 11*b*. For example, with the metal layer 21 being sandwiched between the two dry film resists in the thickness direction of the metal layer 21, predetermined heat and pressure are applied to the three layers, so that the first dry film resist 12 is adhered to the first surface 11*a* of the metal layer 21 and the second dry film resist 13 is adhered to the second surface 11*b*. The first dry film resist 12 and the second dry film resist 13 may be separately adhered to the metal layer 21.

From the viewpoint of enhancing the adhesion between the two dry film resists 12 and 13 and the metal layer 21, preferably each of the first surface 11*a* and the second surface 11*b* of the metal layer 21 is a smooth surface. In that respect, each of the first surface 11*a* and the second surface 11*b* has a specular reflectance of 45.2% or more, so that the adhesion between the dry film resists 12 and 13 and the metal layer 21 can be enhanced to a favorable extent in manufacturing of a metal mask. An intermediate to form a metal mask is thus manufactured.

Figure 9:
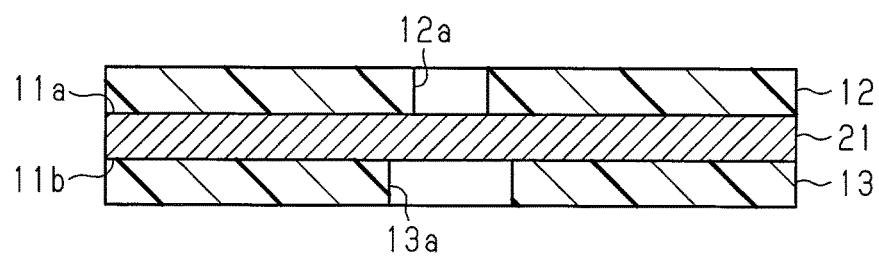
FIG. 9 is a process drawing illustrating a method for manufacturing metal masks, in which a process for developing a dry film resist is shown.

As shown in FIG. 9, the portions of the dry film resists 12 and 13 other than the regions to form through-holes are exposed, and the dry film resist is developed after exposure. As a result, first through-holes 12*a* are formed in the first dry film resist 12, and second through-holes 13*a* are formed in the second dry film resist 13. In other words, the first dry film resist 12 and the second dry film resist 13 are subjected to patterning.

In exposure of the first dry film resist 12, an original plate that allows light to reach portions other than the portions to form the first through-holes 12*a* is placed on the surface opposite to the surface of the first dry film resist 12 in contact with the metal layer 21. In exposure of the second dry film resist 13, an original plate that allows light to reach portions other than the portions to form the second through-holes 13*a* is placed on the surface opposite to the surface of the second dry film resist 13 in contact with the metal layer 21. In development of the dry film resist after exposure, for example, an aqueous solution of sodium carbonate is used as developer.

In the case of first dry film resist 12 formed of positive resist, the portions of the first dry film resist 12 to form the first through-holes 12*a* may be subjected to exposure. In the case of second dry film resist 13 formed of positive resist, the portions of the second dry film resist 13 to form the second through-holes 13*a* may be subjected to exposure.

Figure 10:
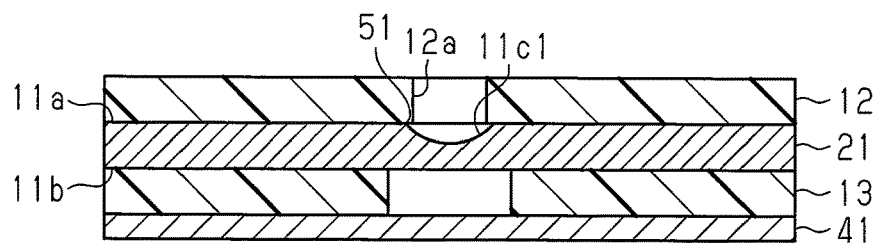
FIG. 10 is a process drawing illustrating a method for manufacturing metal masks, in which a process for etching a first surface of a metal layer is shown.

As shown in FIG. 10, for example, the first surface 11*a* of the metal layer 21 is etched with a solution of ferric chloride through the first dry film resist 12 as mask. On this occasion, a second protective layer 41 is formed on the second dry film resist 13 such that the second surface 11*b* of the metal layer 21 is not etched concurrently with etching of the first surface 11*a*. The material to form the second protective layer 41 may be any material that cannot be easily etched with the solution of ferric chloride. Consequently, first cavities 11c1 depressed toward the second surface 11b are formed in the first surface 11a of the metal layer 21 through the first through-holes 12a of the first dry film resist 12. The first cavity 11c1 has a first opening 51 at the first surface 11a.

The intermediate to form a metal mask described above has enhanced adhesion between the first dry film resist 12 and the metal layer 21. As a result, while the metal layer 21 is exposed to the solution of ferric chloride to come in contact with the first surface 11a of the metal layer 21 through the first through-holes 12a formed in the first dry film resist 12, the solution of ferric chloride is prevented from entering the interface between the first dry film resist 12 and the metal layer 21. The first cavities 11c1 having improved shape accuracy is therefore formed in the metal layer 21.

A plurality of the first cavities 11c1 are formed in the metal layer 21, such that (B/A)×100(%) is 10% or less, where A represents the average dimension of the opening of the first cavities 11c1, in the plan view facing the first surface 11a, and B represents the value obtained by multiplying the standard deviation of the dimension by three.

Figure 11:
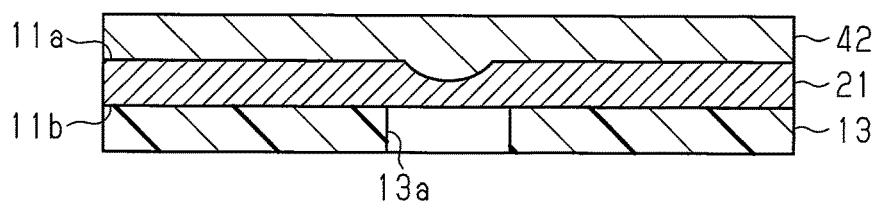
FIG. 11 is a process drawing illustrating a method for manufacturing metal masks, in which a process for forming a first protective layer is shown.

As shown in FIG. 11, the first dry film resist 12 formed on the first surface 11a of the metal layer 21 and the second protective layer 41 in contact with the second dry film resist 13 are removed. In order to prevent the first surface 11a from being etched, a first protective layer 42 is formed on the first surface 11a of the metal layer 21. The material to form the first protective layer 42 may be any material that cannot be easily etched with the solution of ferric chloride.

Figure 12:
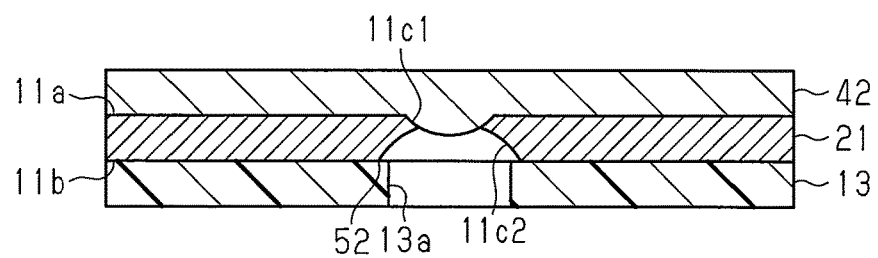
FIG. 12 is a process drawing illustrating a method for manufacturing metal masks, in which a process for etching a second surface of a metal layer is shown.

As shown in FIG. 12, the second surface 11b of the metal layer 21 is etched with a solution of ferric chloride through the second dry film resist 13 as mask. Consequently, second cavities 11c2 depressed toward the first surface 11a are formed in the second surface 11b of the metal layer 21 through the second through-holes 13a of the second dry film resist 13. The second cavity 11c2 has a second opening 52 at the second surface 11b. In the plan view facing the second surface 11b, the second opening 52 is larger than the first opening 51.

The intermediate to form a metal mask described above has enhanced adhesion between the second dry film resist 13 and the metal layer 21 also. As a result, while the metal layer 21 is exposed to the solution of ferric chloride to come in contact with the second surface 11b of the metal layer 21 through the second through-holes 13a formed in the second dry film resist 13, the solution of ferric chloride is prevented from entering the interface between the second dry film resist 13 and the metal layer 21. The second cavities 11c2 having improved shape accuracy is therefore formed in the metal layer 21.

A plurality of the second cavities 11c2 are formed in the metal layer 21, such that (B/A)×100(%) is 10% or less, where A represents the average dimension of the opening of the second cavities 11c2, in the plan view facing the second surface 11b, and B represents the value obtained by multiplying the standard deviation of the dimension by three.

Figure 13:
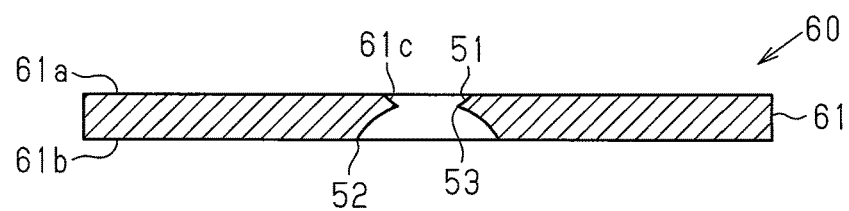
FIG. 13 is a process drawing illustrating a method for manufacturing metal masks, in which a process for removing a dry film resist is shown.

As shown in FIG. 13, the first protective layer 42 and the second dry film resist 13 are removed from the metal layer 21, so that a metal mask 60 having a plurality of through-holes 61c is obtained.

The metal mask 60 comprises a mask substrate 61 as an example of metal mask substrates, which is a processed metal mask substrate 11. The mask substrate 61 includes a first mask surface 61a which corresponds to the first surface 11a, which is a metal surface, of the metal mask substrate 11, with the first dry film resist 12 removed. Also, the mask substrate 61 includes a second mask surface 61b which corresponds to the second surface 11b, which is a metal surface, of the metal mask substrate 11, with the second dry film resist 13 removed.

The through-hole 61c extends through between the first mask surface 61a and the second mask surface 61b, having the minimum cross-sectional area in the direction orthogonal to the direction in which the through-hole 61c extends through the mask substrate 61, between the first mask surface 61a and the second mask surface 61b.

In other words, the through-hole 61c comprises a first opening 51 at the first mask surface 61a, a second opening 52 at the second mask surface 61b, and a narrow part 53 located between the first opening 51 and the second opening 52 in the thickness direction of the mask substrate 61. In the plan view facing the first mask surface 61a, the first opening 51 is smaller than the second opening 52. The shape of the through-hole 61c allows the cross sections to decrease from at the first opening 51 toward the narrow part 53, and from at the second opening 52 toward the narrow part 53. The smaller the distance between the first opening 51 and the narrow part 53, i.e. the distance between the first mask surface 61a and the narrow part 53, the higher the evaluation becomes.

Also, with A representing the average dimension of the first openings 51 in the plan view facing the first mask surface 61a of the metal mask 60, and B representing the value obtained by multiplying the standard deviation of the dimension by three, (B/A)×100(%) is preferably 10% or less. Furthermore, with A representing the average dimension of the second openings 52 in the plan view facing the second mask surface 61b of the metal mask 60, and B representing the value obtained by multiplying the standard deviation of the dimension by three, (B/A)×100(%) is preferably 10% or less.

The metal mask 60 has (B/A)×100(%) of 10% or less, so that the dimensional accuracy is high at the first opening 51 and at the second opening 52 of the through-holes 61c of the metal mask 60.

The first surface 11a of the metal mask substrate 11 may be subjected to various treatments such as washing prior to adhesion to the first dry film resist 12, on the following premise. In that case, the premise means that the various treatments allow each of the specular reflectance, the three-dimensional surface roughness Sa, and the three-dimensional surface roughness Sz of the first mask surface 61a to be maintained at the same values as those of the first surface 11a, i.e. the untreated surface.

The second surface 11b of the metal mask substrate 11 may be subjected to various treatments such as washing prior to adhesion to the second dry film resist 13, on the following premise. In that case, the premise means that the various treatments allow each of the specular reflectance, the three-dimensional surface roughness Sa, and the three-dimensional surface roughness Sz of the second mask surface 61b to be maintained at the same values as those of the second surface 11b, i.e. the untreated surface.

Figure 14:
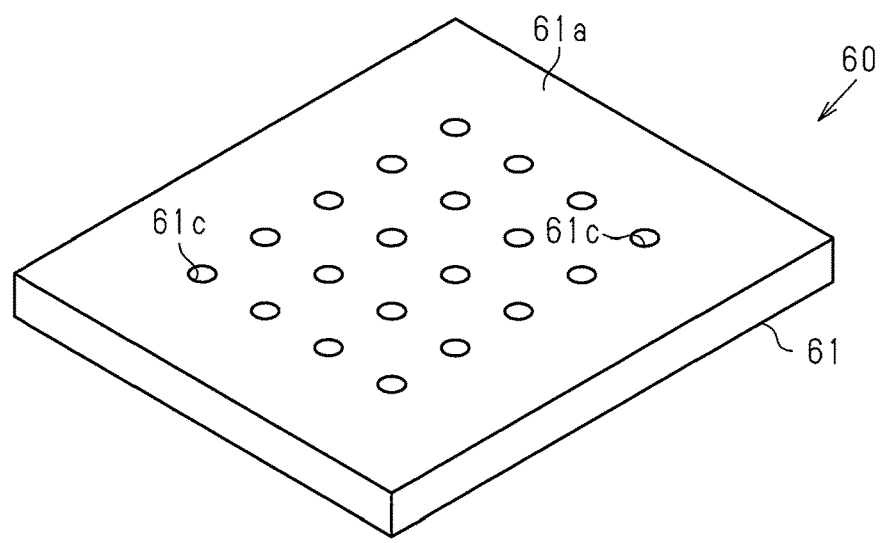
FIG. 14 is a partial perspective view showing a partial perspective structure of a metal mask manufactured using a metal mask substrate for dry film resist.

As shown in FIG. 14, a plurality of through-holes 61c are formed in the mask substrate 61, extending through the mask substrate 61 in the thickness direction, with openings at the first mask surface 61a. For example, in the plan view facing the first mask surface 61a, a plurality of through-holes 61c are regularly arranged in one direction along the first mask surface 61a, and in the direction orthogonal to the one direction.

With the metal mask substrate 11 for use in manufacturing a metal mask in the second mode described above, the intermediate to form a metal mask comprises a metal layer, a resin layer, and a first dry film resist 12. Such an intermediate to form a metal mask may be subjected to etching using the first dry film resist 12 as mask, while the resin layer may be subjected perforation by laser processing or the like.

The mask substrate 61 comprises a metal layer and a resin layer. Such a mask substrate 61 has the first mask surface 61*a* described above, while the surface on the opposite side to the first mask surface 61*a* is not made of metal, being included in the resin layer. Also, in such a structure, preferably a second opening 52 is formed at the first mask surface 61*a*, and a first opening 51 is formed at the surface included in the resin layer.

With the metal mask substrate 11 for use in manufacturing a metal mask in the third mode described above, the intermediate to form a metal mask comprises a resin layer, two metal layers sandwiching the resin layer, and two dry film resists 12 and 14. Such an intermediate to form a metal mask may be subjected to etching using each of the dry film resists 12 and 14 as mask, and in addition to that, the resin layer may be subjected perforation by laser processing or the like.

The mask substrate 61 comprises a resin layer and two metal layers sandwiching the resin layer. In such a mask substrate 61, the first mask surface 61*a* described above is included in one of the metal layers, and the second mask surface 61*b* is included in another one of the metal layers.

The through-holes 61*c* extend through the resin layer and the two metal layers.

EXAMPLES

With reference to FIGS. 15 to 22, Examples will be described below. Hereinafter, a metal mask substrate comprising one metal layer will be described as an example.

<Measurement of Reflectance>
<Minimum of Specular Reflectance>

The reflectance of each of the metal mask substrates in Examples 1 to 4 and Comparative Example 1 were measured by the following measurement method.

Each of the metal mask substrates in Examples 1 to 4 and Comparative Example 1 was obtained by preparing a raw sheet of metal mask substrate having a width of 430 mm and cutting out a part of the raw sheet into a length of 500 mm. The metal mask substrate had a thickness of 20 μm, being formed of invar.

From the cut-out metal mask substrate, a test piece including the center in the width direction and the center in the rolling direction was prepared, having square plate shape with a length in the width direction of the metal mask substrate of 5 cm and a length in the rolling direction of 5 cm.

Each of the test pieces was disposed in the automated goniophotometer (GP-200 manufactured by Murakami Research Laboratory Co., Ltd.), and the reflectance was calculated for the incident light at an angle of 45°±0.2° relative to the normal direction of the measurement surface of the test piece. The reflectance was calculated at each of three measurement spots for one test piece, based on the expression (1) described above.

On this occasion, a region having a diameter of 14 mm in a test piece was exposed to light, and the reflected light was received by a receiving surface having a diameter of 11.4 mm of a receiving part. The receiving part received reflected light having an emitting angle in the range from 0° to 90° at intervals of 0.1°. Each of the test pieces was disposed in the automated goniophotometer, such that the extending direction of the rotation axis A of the receiving part was regarded to be parallel with the rolling direction of the metal mask substrate, or for example, such that the angle formed between the extending direction of the rotation axis A of the receiving part and the rolling direction of the metal mask substrate became within ±2°.

A halogen lamp was used as the light source, and the receiving part for use included a side-on type photomultiplier tube as light receiving device.

Each of the test pieces had three different measurement spots, i.e. a first measurement spot, a second measurement spot, and a third measurement spot, different from each other, and the specular reflectance at each of the first to third measurement spots is shown in Table 1. In each of the test pieces, the first measurement spot was a portion included the center of the test piece, and the second measurement spot and the third measurement spot were different from the first measurement spot, not overlapping each other.

TABLE 1

| | Reflectance (%) | | | |
| --- | --- | --- | --- | --- |
| | First measurement spot | Second measurement spot | Third measurement spot | Minimum |
| Example 1 | 62.6 | 54.4 | 60.2 | 54.4 |
| Example 2 | 48.5 | 45.2 | 49.8 | 45.2 |
| Example 3 | 73.3 | 64.4 | 54.0 | 54.0 |
| Example 4 | 83.2 | 74.0 | 85.8 | 74.0 |
| Comparative Example 1 | 25.8 | 25.4 | 30.0 | 25.4 |

As shown in Table 1, it was found that the reflectance was 62.6% at the first measurement spot, 54.4% at the second measurement spot, and 60.2% at the third measurement spot in Example 1. In other words, it was found that the minimum of the specular reflectance was 54.4% in Example 1.

It was found that the reflectance was 48.5% at the first measurement spot, 45.2% at the second measurement spot, and 49.8% at the third measurement spot in Example 2. In other words, it was found that the minimum of the specular reflectance was 45.2% in Example 2.

It was found that the reflectance was 73.3% at the first measurement spot, 64.4% at the second measurement spot, and 54.0% at the third measurement spot in Example 3. In other words, it was found that the minimum of the specular reflectance was 54.0% in Example 3.

It was found that the reflectance was 83.2% at the first measurement spot, 74.0% at the second measurement spot, and 85.8% at the third measurement spot in Example 4. In other words, it was found that the minimum of the specular reflectance was 74.0% in Example 4.

It was found that the reflectance was 25.8% at the first measurement spot, 25.4% at the second measurement spot, and 30.0% at the third measurement spot in Comparative Example 1. In other words, it was found that the minimum of the specular reflectance was 25.4% in Comparative Example 1.

<Difference Between First Reflectance and Second Reflectance>

From each of the metal mask substrates in Example 5 and Comparative Example 2, four sheets of test pieces were prepared. In the same manner as in Example 1, each of the metal mask substrates in Example 5 and Comparative Example 2 was obtained by preparing a raw sheet of metal mask substrate having a width of 430 mm and cutting out a part of the raw sheet into a length of 500 mm. From each of four arbitrary positions in the cut-out metal mask substrate, a test piece was cut out. Each of the test pieces had a square plate shape with a length in the width direction of the metal mask substrate of 5 cm and a length in the rolling direction of 5 cm in the same manner as in Example 1.

For calculation of the reflectance, each of the test pieces was disposed in the automated goniophotometer such that the extending direction of the rotation axis A of the receiving part was regarded to be parallel with the rolling direction of the metal mask substrate, or for example, such that the angle formed between the extending direction of the rotation axis A of the receiving part and the rolling direction of the metal mask substrate became within ±2°. In other words, the first reflectance as the reflectance in a first plane orthogonal to the surface of the metal mask substrate and orthogonal to the rolling direction was calculated.

Each of the test pieces was disposed in the automated goniophotometer such that the extending direction of the rotation axis A of the receiving part was regarded to be parallel with the width direction of the metal mask substrate, or for example, such that the angle formed between the extending direction of the rotation axis A of the receiving part and the width direction of the metal mask substrate became within ±2°. In other words, the second reflectance as the reflectance in a second plane orthogonal to the surface of the metal mask substrate and orthogonal to the width direction was calculated.

The incident light to each of the test pieces were provided under the same conditions described above. In both of the calculations of the first reflectance and the second reflectance, the center of each of the test pieces was exposed to light. For each of the test pieces, the reflectance at a region exposed to light was calculated based on the expression (1) described above.

The first reflectance and the second reflectance for each of the test pieces were the values shown in Table 2.

of 29.5% in Comparative Example 2. It was found that the test piece 3 had a first reflectance of 33.1% and a second reflectance of 32.8%, and the test piece 4 had a first reflectance of 34.0% and a second reflectance of 31.7%.

It was found that the difference obtained by subtracting the first reflectance from the second reflectance was 1.3% in the test piece 1, −3.8% in the test piece 2, −0.3% in the test piece 3, and −2.3% in the test piece 4. In other words, it was found that a portion in which the second reflectance was larger than the first reflectance and a portion in which the second reflectance was smaller than the first reflectance were included in Comparative Example 2. It was also found that any portion included in Comparative Example 2 had a smaller difference obtained by subtracting the first reflectance from the second reflectance than in Example 5.

<Measurement of Surface Roughness>

The three-dimensional surface roughness Sa and the three-dimensional surface roughness Sz of each of the metal mask substrates in Examples 1 to 4 and Comparative Example 1 were measured by the following measurement method.

Using a shape measurement laser microscope having an object lens with a magnification of 50× (VK-X210, manufactured by Keyence Corporation), the three-dimensional surface roughness Sa and the three-dimensional surface roughness Sz were measured. As the three-dimensional surface roughness Sa and the three-dimensional surface roughness Sz, the three-dimensional surface roughness Sa and the three-dimensional surface roughness Sz of a surface having a width of about 280 µm in one direction and a width of about 220 µm in the direction orthogonal to the one direction were measured.

The three-dimensional surface roughness Sa and the three-dimensional surface roughness Sz were measured in the method in accordance with ISO 25178.

TABLE 2

|  | Reflectance (%) | Test piece 1 | Test piece 2 | Test piece 3 | Test piece 4 | Minimum |
|---|---|---|---|---|---|---|
| Example 5 | First reflectance | 75.9 | 56.1 | 62.8 | 64.8 | 56.1 |
|  | Second reflectance | 77.8 | 67.9 | 73.0 | 78.5 | 67.9 |
|  | Difference | 1.9 | 11.8 | 10.2 | 13.7 |  |
| Comparative | First reflectance | 30.1 | 33.3 | 33.1 | 34.0 | 30.1 |
| Example 2 | Second reflectance | 31.4 | 29.5 | 32.8 | 31.7 | 29.5 |
|  | Difference | 1.3 | −3.8 | −0.3 | −2.3 |  |

As shown in Table 2, it was found that the test piece 1 had a first reflectance of 75.9% and a second reflectance of 77.8%, and the test piece 2 had a first reflectance of 56.1% and a second reflectance of 67.9% in Example 5. It was found that the test piece 3 had a first reflectance of 62.8% and a second reflectance of 73.0%, and the test piece 4 had a first reflectance of 64.8% and a second reflectance of 78.5%.

It was found that the difference obtained by subtracting the first reflectance from the second reflectance was 1.9% in the test piece 1, 11.8% in the test piece 2, 10.2% in the test piece 3, and 13.7% in the test piece 4. In other words, it was found that the second reflectance was larger than the first reflectance in Example 5. It was also found that a portion having a difference obtained by subtracting the first reflectance from the second reflectance of 10.2% or more was included in Example 5.

It was found that the test piece 1 had a first reflectance of 30.1% and a second reflectance of 31.4%, and the test piece 2 had a first reflectance of 33.3% and a second reflectance The metal mask substrates in Examples 1 to 4 and Comparative Example 1 were obtained by preparing a raw sheet of metal mask substrate having a width of 430 mm and cutting out a part of the raw sheet into a length of 500 mm in the same manner as in measurement of the reflectance.

From three places different from each other of each of the metal mask substrates in Examples 1 to 4 and Comparative Example 1, test pieces were cut out, respectively, so as to be subjected to measurement of the surface roughness. Each of the test pieces had a rectangular shape with a length in the rolling direction of the metal mask substrate of 20 mm, and a length in the width direction of the metal mask substrate of 30 mm.

The two ends of a metal mask substrate in the rolling direction were defined as a first end and a second end. The two ends of a metal mask substrate in the width direction were defined as a third end and a fourth end. Three test pieces were cut out from the following positions of a metal mask substrate.

Specifically, a test piece 1 was cut out at the position 100 mm away from the first end and 200 mm away from the third end. A test piece 2 was cut out at the position 100 mm away from the second end and 70 mm away from the third position. A test piece 3 was cut out at the position 100 mm away from the second end and 70 mm away from the fourth end.

The three-dimensional surface roughness Sa and the three-dimensional surface roughness Sz were measured at five measurement spots of each of the test pieces. The five measurement spots included one spot at the center and four spots at the periphery around the one spot of each of the test pieces. The four spots at the periphery of each of the test pieces were positioned on the diagonal lines of the test piece, and the distance between the one point at the center and each of the points at the periphery was set at 10 mm.

In each of Examples 1 to 4 and Comparative Example 1, the maximum of the three-dimensional surface roughness Sa and the maximum of the three-dimensional surface roughness Sz of each of the test pieces were the values shown in Table 3.

TABLE 3

|  |  | Sa | Sz |
|---|---|---|---|
| Example 1 | Test piece 1 | 0.09 | 2.83 |
|  | Test piece 2 | 0.08 | 2.63 |
|  | Test piece 3 | 0.09 | 3.17 |
| Example 2 | Test piece 1 | 0.10 | 2.93 |
|  | Test piece 2 | 0.11 | 2.84 |
|  | Test piece 3 | 0.10 | 2.96 |
| Example 3 | Test piece 1 | 0.07 | 1.88 |
|  | Test piece 2 | 0.07 | 1.56 |
|  | Test piece 3 | 0.06 | 1.90 |
| Example 4 | Test piece 1 | 0.08 | 2.06 |
|  | Test piece 2 | 0.06 | 1.41 |
|  | Test piece 3 | 0.06 | 1.56 |
| Comparative Example 1 | Test piece 1 | 0.14 | 5.10 |
|  | Test piece 2 | 0.13 | 5.78 |
|  | Test piece 3 | 0.16 | 5.10 |

As shown in Table 3, it was found that the test piece 1 had a maximum of three-dimensional surface roughness Sa of 0.09 µm, and a maximum of three-dimensional surface roughness Sz of 2.83 µm, in Example 1. It was found that the test piece 2 had a maximum of three-dimensional surface roughness Sa of 0.08 µm, and a maximum of three-dimensional surface roughness Sz of 2.63 µm; and the test piece 3 had a maximum of three-dimensional surface roughness Sa of 0.09 µm, and a maximum of three-dimensional surface roughness Sz of 3.17 µm. In other words, it was found that the maximum of the three-dimensional surface roughness Sa was 0.09 µm and the maximum of the three-dimensional surface roughness Sz was 3.17 µm, in Example 1.

It was found that the test piece 1 had a maximum of three-dimensional surface roughness Sa of 0.10 µm, and a maximum of three-dimensional surface roughness Sz of 2.93 µm, in Example 2. It was found that the test piece 2 had a maximum of three-dimensional surface roughness Sa of 0.11 µm, and a maximum of three-dimensional surface roughness Sz of 2.84 µm; and the test piece 3 had a maximum of three-dimensional surface roughness Sa of 0.10 µm, and a maximum of three-dimensional surface roughness Sz of 2.96 µm. In other words, it was found that the maximum of the three-dimensional surface roughness Sa was 0.11 µm and the maximum of the three-dimensional surface roughness Sz was 2.96 µm, in Example 2.

It was found that the test piece 1 had a maximum of three-dimensional surface roughness Sa of 0.07 µm, and a maximum of three-dimensional surface roughness Sz of 1.88 µm, in Example 3. It was found that the test piece 2 had a maximum of three-dimensional surface roughness Sa of 0.07 µm, and a maximum of three-dimensional surface roughness Sz of 1.56 µm; and the test piece 3 had a maximum of three-dimensional surface roughness Sa of 0.06 µm, and a maximum of three-dimensional surface roughness Sz of 1.90 µm. In other words, it was found that the maximum of the three-dimensional surface roughness Sa was 0.07 µm and the maximum of the three-dimensional surface roughness Sz was 1.90 µm, in Example 3.

It was found that the test piece 1 had a maximum of three-dimensional surface roughness Sa of 0.08 µm, and a maximum of three-dimensional surface roughness Sz of 2.06 µm, in Example 4. It was found that the test piece 2 had a maximum of three-dimensional surface roughness Sa of 0.06 µm, and a maximum of three-dimensional surface roughness Sz of 1.41 µm; and the test piece 3 had a maximum of three-dimensional surface roughness Sa of 0.06 µm, and a maximum of three-dimensional surface roughness Sz of 1.56 µm. In other words, it was found that the maximum of the three-dimensional surface roughness Sa was 0.08 µm and the maximum of the three-dimensional surface roughness Sz was 2.06 µm, in Example 4.

It was found that the test piece 1 had a maximum of three-dimensional surface roughness Sa of 0.14 µm, and a maximum of three-dimensional surface roughness Sz of 5.10 µm, in Comparative Example 1. It was found that the test piece 2 had a maximum of three-dimensional surface roughness Sa of 0.13 µm, and a maximum of three-dimensional surface roughness Sz of 5.78 µm; and the test piece 3 had a maximum of three-dimensional surface roughness Sa of 0.16 µm, and a maximum of three-dimensional surface roughness Sz of 5.10 µm. In other words, it was found that the maximum of the three-dimensional surface roughness Sa was 0.16 µm and the maximum of the three-dimensional surface roughness Sz was 5.78 µm, in Comparative Example 1.

<Evaluation>

Figure 15:
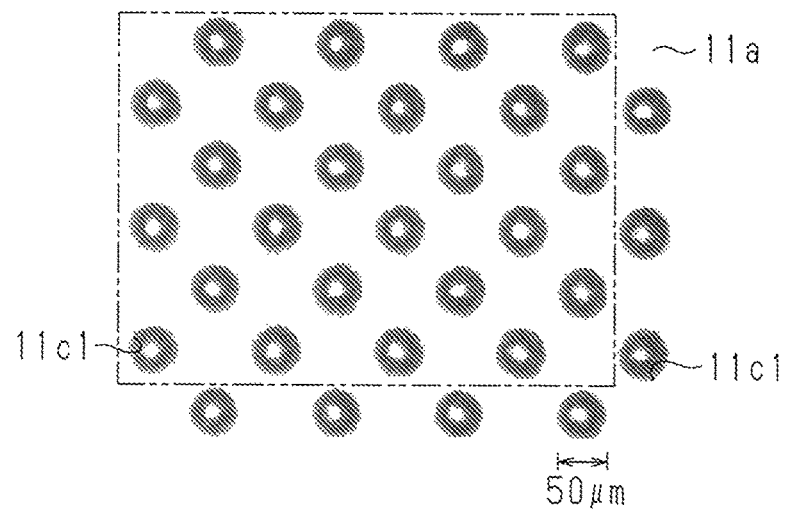
FIG. 15 is a picture showing a photographed first surface having a plurality of first cavities in Example 1.

In the step of manufacturing a metal mask from the metal mask substrate in Example 1, first cavities were formed in the first surface. The first surface was then irradiated with light. FIG. 15 is a picture showing the photographed reflection light reflected from the first surface.

Figure 16:
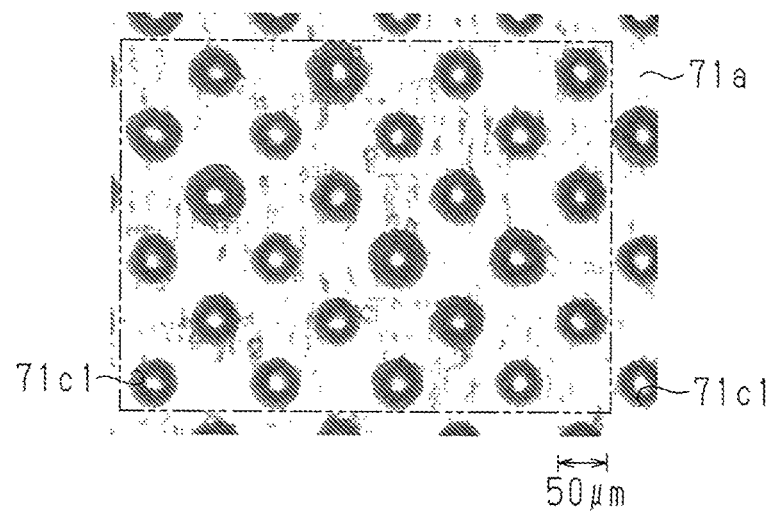
FIG. 16 is a picture showing a photographed surface having a plurality of first cavities in Comparative Example 1.

In the step of manufacturing a metal mask from the metal mask substrate in Comparative Example 1, first cavities were formed in the first surface. The first surface was then irradiated with light. FIG. 16 is a picture showing the photographed reflection light reflected from the first surface.

As shown in FIG. 15, the metal mask substrate 11 in Example 1 allowed the adhesion between the metal mask substrate 11 and the first dry film resist 12 to be enhanced. It was therefore found that the size of the opening of each of the first cavities 11c1 at the first surface 11a was approximately equal to the size of opening of all the other first cavities 11c1, in the plan view facing the first surface 11a.

On the other hand, it was found that as shown in FIG. 16, in the plan view facing the metal layer surface 71a of the metal mask substrate in Comparative Example 1, the size of opening of a plurality of the first cavities 71c1 varied widely.

The diameter of twenty-four pieces of the first cavities of each of the metal mask substrates in Example 1 and Comparative Example 1 was measured. In Example 1, among the first cavities 11c1 shown in FIG. 15, the first cavities 11c1 included in the region surrounded by the two-dot chain lines were subjected to measurement of the diameter. In Comparative Example 1, among the first cavities 71c1 shown in FIG. 16, the first cavities 71c1 included in the region surrounded by the two-dot chain lines were subjected to measurement of the diameter.

Also, each of the first cavities was subjected to measurement of a first diameter, i.e. the diameter in the orthogonal direction of the page, and a second diameter, i.e. the diameter in the horizontal direction of the page. The average of the first diameter and the second diameter, i.e. the average diameter, of each of the first cavities was then calculated. The first diameter, the second diameter, and the average diameter in Example 1, and the first diameter, the second diameter, and the average diameter in Comparative diameter 1 were as shown in Table 4.

Since (B/A)×100(%) was 8.2% or less, i.e. 10% or less, in Example 1, it was found that not only the opening of the first cavities 11c1 of the metal mask substrate 11, but also the diameter at the opening of the through-holes of the metal mask had high dimensional accuracy. In contrast thereto, (B/A)×100(%) was 30.3% or less in Comparative Example 1. It was therefore found that the dimensional accuracy of not only the opening of the first cavities 11c1 of the metal mask substrate 11, but also of the diameter at the opening of the through-holes of the metal mask were greatly improved in Example 1, in comparison with in Comparative Example 1.

TABLE 4

| | Example 1 | | | Comparative Example 1 | | |
|---|---|---|---|---|---|---|
| Number | First diameter | Second diameter | Average diameter | First diameter | Second diameter | Average diameter |
| 1 | 48.8 | 49.2 | 49.0 | 46.8 | 53.2 | 50.0 |
| 2 | 50.4 | 48.0 | 49.2 | 64.1 | 65.7 | 64.9 |
| 3 | 48.8 | 49.2 | 49.0 | 55.2 | 52.8 | 54.0 |
| 4 | 50.4 | 50.0 | 50.2 | 53.2 | 53.6 | 53.4 |
| 5 | 47.2 | 48.4 | 47.8 | 56.5 | 57.7 | 57.1 |
| 6 | 47.6 | 48.0 | 47.8 | 48.4 | 53.2 | 50.8 |
| 7 | 50.8 | 47.2 | 49.0 | 46.8 | 50.8 | 48.8 |
| 8 | 51.2 | 48.8 | 50.0 | 49.6 | 56.5 | 53.0 |
| 9 | 48.8 | 49.2 | 49.0 | 64.5 | 60.5 | 62.5 |
| 10 | 47.2 | 47.2 | 47.2 | 52.4 | 50.8 | 51.6 |
| 11 | 51.2 | 48.0 | 49.6 | 55.2 | 57.3 | 56.3 |
| 12 | 49.2 | 49.2 | 49.2 | 55.2 | 54.8 | 55.0 |
| 13 | 48.8 | 48.4 | 48.6 | 52.4 | 48.4 | 50.4 |
| 14 | 47.6 | 49.2 | 48.4 | 50.8 | 52.4 | 51.6 |
| 15 | 49.2 | 49.2 | 49.2 | 59.3 | 57.3 | 58.3 |
| 16 | 49.6 | 49.2 | 49.4 | 60.5 | 62.5 | 61.5 |
| 17 | 47.2 | 46.8 | 47.0 | 50.4 | 49.2 | 49.8 |
| 18 | 50.4 | 49.6 | 50.0 | 47.6 | 47.6 | 47.6 |
| 19 | 49.6 | 51.2 | 50.4 | 54.8 | 58.5 | 56.7 |
| 20 | 50.4 | 48.4 | 49.4 | 45.2 | 52.8 | 49.0 |
| 21 | 47.6 | 49.2 | 48.4 | 44.4 | 47.6 | 46.0 |
| 22 | 47.2 | 47.2 | 47.2 | 52.4 | 50.4 | 51.4 |
| 23 | 49.2 | 50.8 | 50.0 | 53.2 | 51.6 | 52.4 |
| 24 | 50.4 | 48.8 | 49.6 | 49.2 | 48.4 | 48.8 |
| Average | 49.1 | 48.8 | 48.9 | 52.8 | 53.9 | 53.4 |
| Maximum | 51.2 | 51.2 | 50.4 | 64.5 | 65.7 | 64.9 |
| Minimum | 47.2 | 46.8 | 47.0 | 44.4 | 47.6 | 46.0 |
| Standard deviation | 1.34 | 1.07 | 0.96 | 5.34 | 4.69 | 4.75 |

As shown in Table 4, it was found that the average diameter of the first cavities 11c1 in Example 1 was 47.0 μm or more and 50.4 μm or less, and the average diameter of the first cavities 71c1 in Comparative Example 1 was 46.0 μm or more and 64.9 μm or less.

In Example 1, with A representing the average diameter of the first cavities 11c1 at opening in the plan view facing the surface of the metal mask substrate 11, and B representing the value obtained by multiplying the standard deviation of the diameter by three, (B/A)×100(%) was calculated. It was found that the first diameter had (B/A)×100(%) of 8.2%, the second diameter had (B/A)×100(%) of 6.6%, and the average diameter had (B/A)×100(%) of 5.9%.

In Comparative Example 1, (B/A)×100(%) was calculated, where A represents the average diameter of the first cavities 71c1 at opening in the plan view facing the metal layer surface 71a, and B represents the value obtained by multiplying the standard deviation of the diameter by three, as in Example 1. It was found that the first diameter had (B/A)×100(%) of 30.3%, the second diameter had (B/A)×100(%) of 26.1%, and the average diameter had (B/A)×100(%) of 26.7%.

Also, in Example 1 and Comparative Example 1, a histogram showing the frequency of average diameter of the first cavities at intervals of 2 μm, and a histogram at intervals of 1 μm were made.

Figure 17:
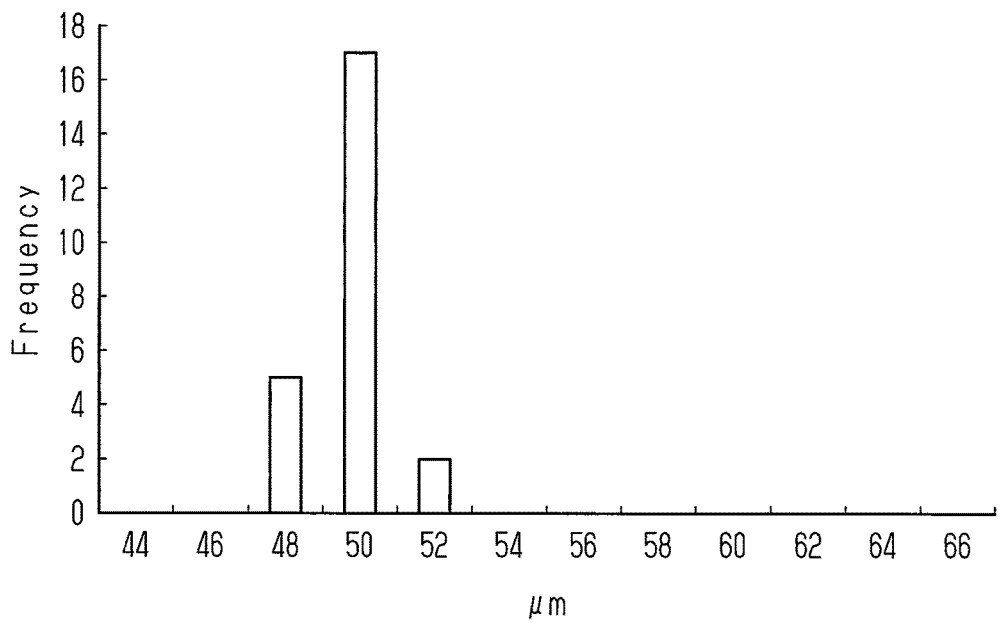
FIG. 17 is a histogram showing the diameter distribution of first cavities at intervals of 2 µm in Example 1.
Figure 18:
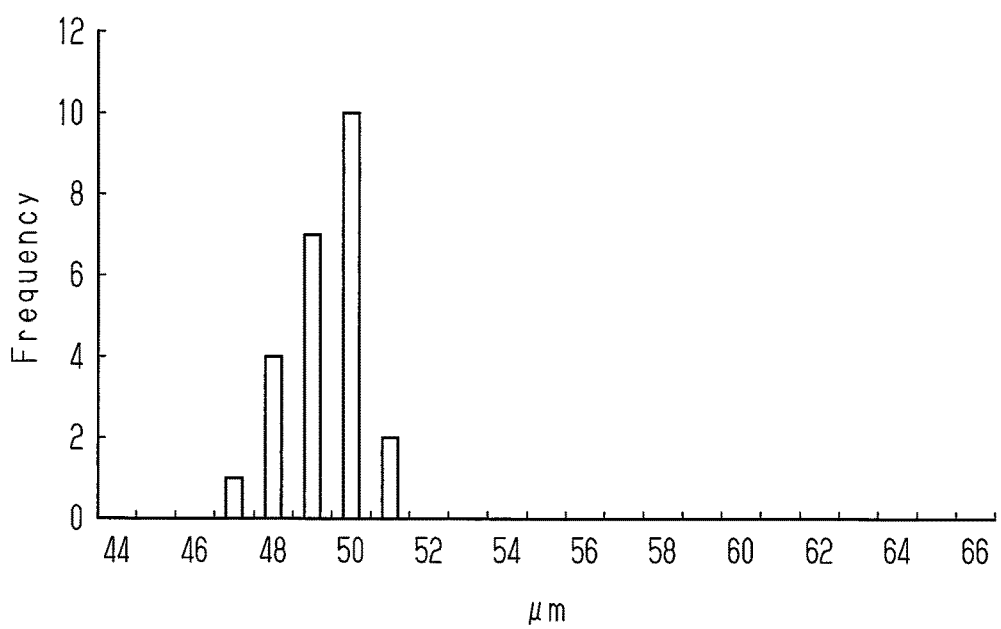
FIG. 18 is a histogram showing the diameter distribution of first cavities at intervals of 1 µm in Example 1.
Figure 19:
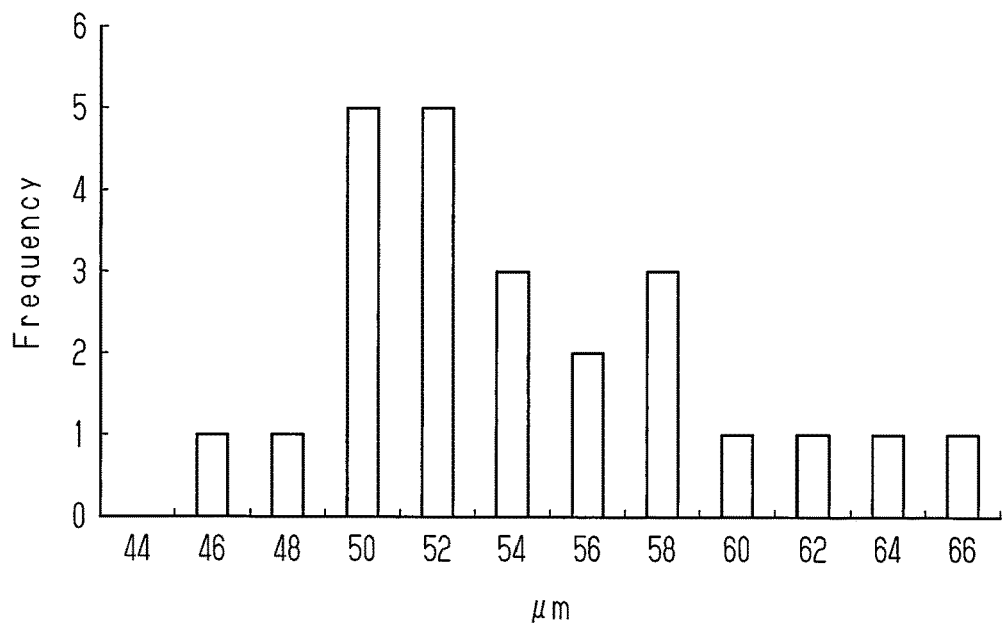
FIG. 19 is a histogram showing the diameter distribution of first cavities at intervals of 2 µm in Comparative Example 1.
Figure 20:
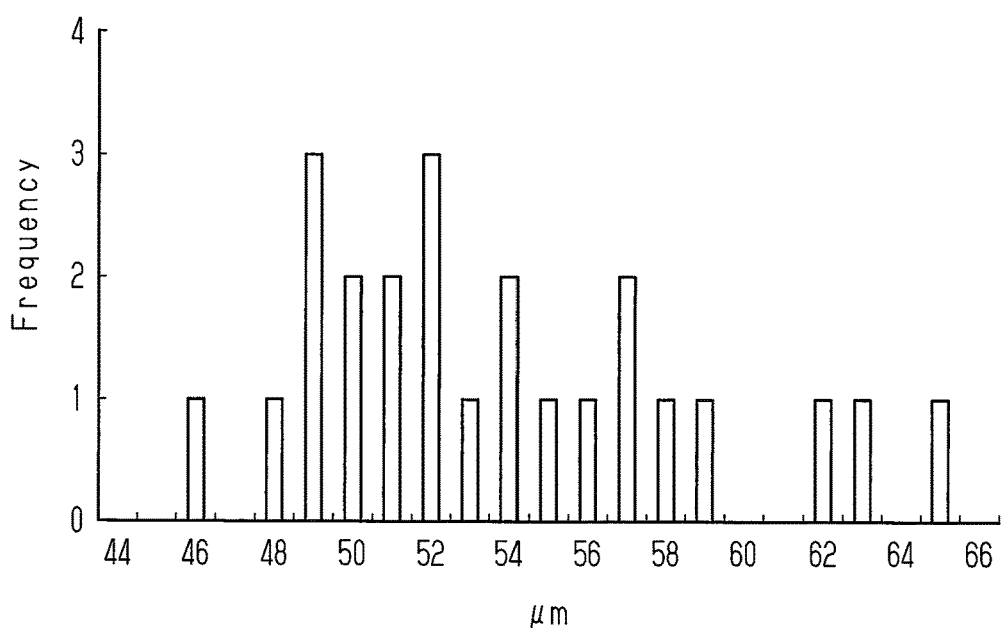
FIG. 20 is a histogram showing the diameter distribution of first cavities at intervals of 1 µm in Comparative Example 1.

As shown in FIGS. 17 and 18, it was found that, in Example 1, the frequency of the average diameter of the first cavities was the highest at 50 μm. Also, as shown in FIGS. 19 and 20, it was found that the difference in the frequency of each of the average diameter values in Comparative Example 1 was smaller than in Example 1.

It was therefore found that the metal mask substrate 11 in Example 1 allowed the adhesion between the metal mask substrate 11 and the first dry film resist 12 to be enhanced, so that each of the first cavities 11c1 was formed with high shape accuracy. On the other hand, it was found that the metal mask substrate in Comparative Example 1 had low adhesion between the metal mask substrate and the dry film resist, so that a plurality of the first cavities 71c1 had low shape accuracy.

It was found that in each of Examples 2 to 5, a shape equivalent to the shapes of the first cavities shown in FIG. 15 was obtained. In other words, it was found that as long as one surface of the metal mask substrate 11 had a specular reflectance of 45.2% or more, the adhesion between the metal layer 21 and the first dry film resist 12 was enhanced.

Also, in forming the second cavities 11c2 in the second surface 11b of the metal mask substrate 11, as long as the specular reflectance at the second surface 11b was in the range described above, the following tendency was found. Specifically, as with forming the first cavities 11c1 in the first surface 11a of the metal mask substrate 11, the tendency to have enhanced adhesion between the metal mask substrate 11 and the second dry film resist 13 was found.

<Correlation Between Reflectance and Surface Roughness>
<Reflectance and Three-dimensional Surface Roughness Sa>

The correlation between the minimum of specular reflectance and the maximum of three-dimensional surface roughness Sa is shown below as the results of regression analysis. In the regression analysis, the measurement results in Examples 1 to 4 and Comparative Example 1 were used. With the three-dimensional surface roughness Sa as explanatory variable, and with the specular reflectance as explained variable, the regression equation between the minimum of specular reflectance and the maximum of three-dimensional surface roughness Sa was calculated using the least squares method.

Figure 21:
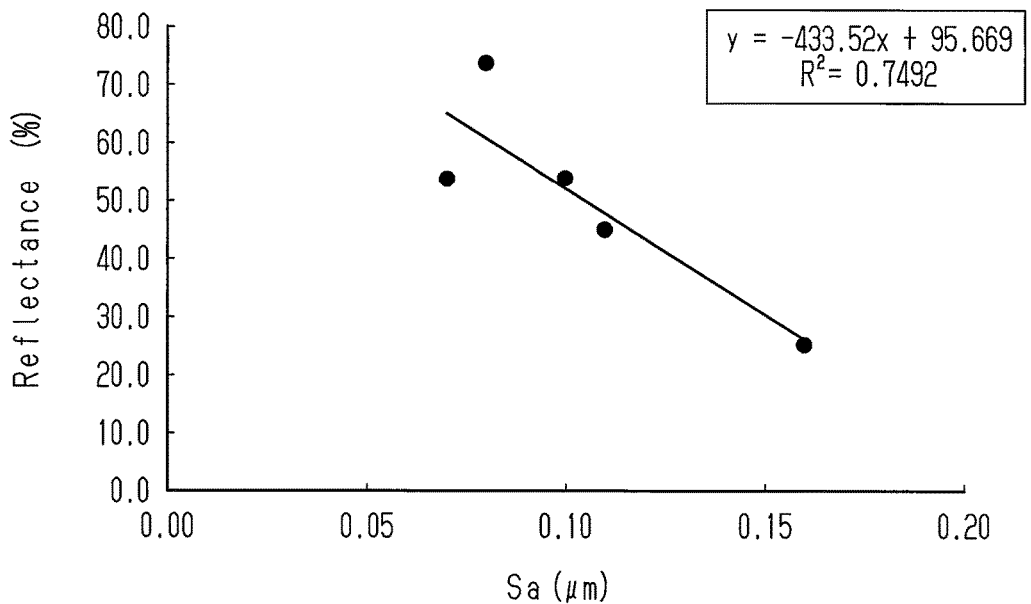
FIG. 21 is a graph showing the correlation between three-dimensional surface roughness Sa and specular reflectance.

As shown in FIG. 21, the regression equation was represented by y=−433.52x+95.669, and the coefficient of determination $R^2$ was found to be 0.7492. In other words, a strong correlation between the minimum of specular reflectance and the maximum of three-dimensional surface roughness Sa was found.

<Reflectance and Three-dimensional Surface Roughness Sz>

The correlation between the minimum of specular reflectance and the maximum of three-dimensional surface roughness Sz is shown below as regression analysis results. In the regression analysis, the measurement results in Examples 1 to 4 and Comparative Example 1 were used. With the three-dimensional surface roughness Sz as explanatory variable, and with the specular reflectance as explained variable, the regression equation between the minimum of specular reflectance and the maximum of three-dimensional surface roughness Sz was calculated using the least squares method.

Figure 22:
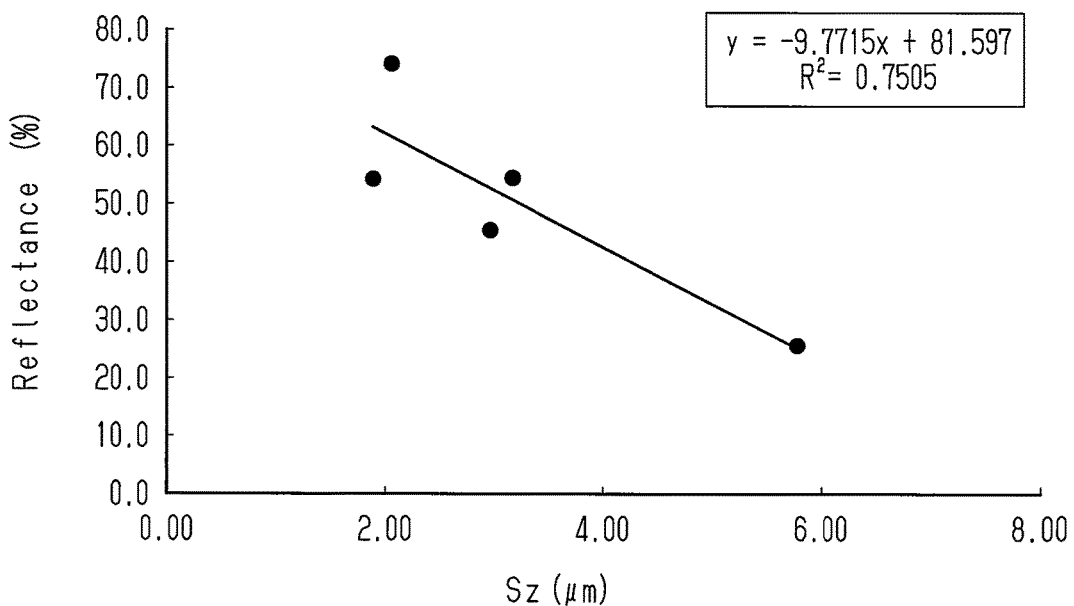
FIG. 22 is a graph showing the correlation between three-dimensional surface roughness Sz and specular reflectance.

As shown in FIG. 22, the regression equation was represented by y=−9.7715x+81.597, and the coefficient of determination $R^2$ was found to be 0.7505. In other words, a strong correlation between the minimum of specular reflectance and the maximum of three-dimensional surface roughness Sz was found.

As described above, it was found that the specular reflectance had negative correlations with each of the three-dimensional surface roughness Sa and the three-dimensional surface roughness Sz. It was also found that as long as the specular reflectance was 45.2% or more, both of the values of the three-dimensional surface roughness Sa and the three-dimensional surface roughness Sz allowed the adhesion at the interface between the dry film resist and the metal mask substrate for dry film resist to be enhanced. In other words, it was found that as the three-dimensional surface roughness Sa decreased, the specular reflectance increased; and as the three-dimensional surface roughness Sz decreased, the specular reflectance increased.

Accordingly, in order to enhance the adhesion at the interface between the dry film resist and the metal mask substrate for dry film resist, the surface state of the metal mask substrate for dry film resist can be controlled through the measured values of specular reflectance.

As described above, through the embodiment of a metal mask substrate for dry film resist, a method for controlling metal mask substrates for dry film resist, a metal mask, and a method for manufacturing metal masks, the advantages listed below are obtained.

(1) The incident light to the first surface 11a has a specular reflectance of 45.2% or more, so that the adhesion at the interface between the first surface 11a of the metal mask substrate 11 and the first dry film resist 12 is enhanced.

(2) The relatively small reflectance of the two reflectances obtained at the first surface 11a is 45.2% or more, so that the adhesion at the interface between the first surface 11a of the metal mask substrate 11 and the first dry film resist 12 is more enhanced.

(3) The first surface 11a includes a portion having the second reflectance larger than the first reflectance by 10.2% or more, so that the adhesion at the interface between the first surface 11a and the dry film resist 12 is more easily enhanced.

(4) With a specular reflectance of 45.2% or more at the surface of the metal mask substrate 11, the three-dimensional surface roughness Sa is 0.11 μm or less and the three-dimensional surface roughness Sz is 3.17 μm or less, so that the adhesion at the interface between the first dry film resist 12 and the first surface 11a is more reliably enhanced.

(5) In the first mode and the third mode, the adhesion between the first surface 11a and the first dry film resist 12 and the adhesion between the second surface 11b and the second dry film resists 13 and 14 are enhanced, so that the processing accuracy in etching of the first surface 11a and the second surface 11b is improved.

(6) The linear expansion coefficient of a glass substrate is almost equivalent to the linear expansion coefficient of invar, so that a metal mask 60 formed from the metal mask substrate 11 can be applied to film formation on a glass substrate. In other words, a metal mask 60 having improved shape accuracy can be applied to film formation on a glass substrate.

The embodiment described above may be appropriately modified as follows.

The material to form the metal layer 21 may be other than invar, as long as the material is pure metal or alloy having a surface with metallic luster. In the case of the metal layer 21 made of material other than invar, the resin layer in contact with the metal layer 21 may be formed of resin having a difference in linear expansion coefficient between the material to form the metal layer 21 and the resin smaller than the difference in linear expansion coefficient between the material to form the metal layer 21 and polyimide.

The metal layers 21 and 23 may have a second surface 11b at which the second reflectance is larger than the first reflectance, with the first reflectance being 45.2% or more. With such a structure, the second surface 11b achieves the similar advantage as in the first surface 11a of the metal layer 21 having the second reflectance larger than the first reflectance, with the first reflectance being 45.2% or more.

The second surface 11b may include a portion having a difference obtained by subtracting the first reflectance from the second reflectance of 10.2% or more. With such a structure, the second surface 11b achieves the similar advantage as in the first surface 11a including a portion having a difference obtained by subtracting the first reflectance from the second reflectance of 10.2% or more.

The metal layers 21 and 23 may have a specular reflection of less than 45.2% at the second surface 11b. Even such a structure enhances the adhesion between the metal layer 21 and the first dry film resist 12 at least at the first surface 11a.

As described above, the measurement region of the three-dimensional surface roughness is significantly smaller than the measurement region of the reflectance. From the viewpoint of enhancing the adhesion between the surface of the metal mask substrate and the dry film resist in a microscopic range corresponding to the size of measurement region of the three-dimensional surface roughness, it is effective to have a three-dimensional surface roughness Sz of 3.17 μm or less. It is also effective to have a three-dimensional surface roughness Sa of 0.11 μm or less. However, from the viewpoint of macroscopically enhancing the adhesion between the surface of the metal mask substrate and the dry film resist, an advantage corresponding to the item (1) described above is obtained, for example, at the first surface 11a of the metal mask substrate 11, as long as the specular reflectance is 45.2% or more even with a surface roughness Sz of larger than 3.17 μm. The same is true of the three-dimensional surface roughness Sa, so that an advantage corresponding to the item (1) described above is obtained, as long as the specular reflectance is 45.2% or more even with a three-dimensional surface roughness Sa of larger than 0.11 μm.

As long as the first surface 11a of the metal mask substrate 11 has a surface roughness at a degree with difficulty in identifying the rolling direction from the first reflectance value and the second reflectance value, and both of the first reflectance and the second reflectance are 45.2% or more, the portion having a difference obtained by subtracting the first reflectance from the second reflectance of 10.2% or more may not be included. Even with such a structure, an advantage corresponding to the item (1) described above is obtained.

As long as the first surface 11a of the metal mask substrate 11 has a surface roughness at a degree with difficulty in identifying the rolling direction from the first reflectance value and the second reflectance value, and both of the first reflectance and the second reflectance are 45.2% or more, a portion having the first reflectance and the second reflectance at about the same degree, or a portion having the first reflectance larger than the second reflectance may be included. Even with such a structure, an advantage corresponding to the item (1) described above is obtained.

The cross-sectional area of each of the through-holes 61c may be about the same entirely in the thickness direction of the mask substrate 61. Alternatively, the cross-sectional area of each of the through-holes 61c may increase in the thickness direction from the first mask surface 61a toward the second mask surface 61b, or may decrease from the first mask surface 61a toward the second mask surface 61b.

The metal mask 60 is not limited to a metal mask for use in vapor deposition, on a glass substrate, of a material for forming organic EL devices, and may be a metal mask for other applications such as film formation by vapor deposition or sputtering of various metal materials. In that case, the through-holes 61c may be irregularly arranged in the plan view facing the first mask surface 61a.

The resist for use in etching of metal mask substrates is not limited to the dry film resist, and may be a resist formed by applying a coating liquid to form resist onto a metal mask substrate. In other words, the resist may be disposed on the surface of a metal mask substrate by coating, or may be disposed on the surface of a metal mask substrate by adhesion. Even with such a resist having low adhesion to the surface of a metal mask substrate, the metal mask substrate described above achieves the similar advantage as using a dry film resist.

DESCRIPTION OF THE REFERENCE NUMERALS

10: INTERMEDIATE TO FORM METAL MASK
11: METAL MASK SUBSTRATE
11a: FIRST SURFACE
11b: SECOND SURFACE
11c1, 71c1: FIRST CAVITY
11c2: SECOND CAVITY
12: FIRST DRY FILM RESIST
12a: FIRST THROUGH-HOLE
13, 14: SECOND DRY FILM RESIST
13a: SECOND THROUGH-HOLE
21, 23: METAL LAYER
21a: BASE MATERIAL
21b: ROLLED MATERIAL
22: RESIN LAYER
30: ROLLING DEVICE
31, 32: ROLLER
33: ANNEALING DEVICE
41: SECOND PROTECTIVE LAYER
42: FIRST PROTECTIVE LAYER
51: FIRST OPENING
52: SECOND OPENING
53: NARROW PART
60: METAL MASK
61: MASK SUBSTRATE
61a: FIRST MASK SURFACE
61b: SECOND MASK SURFACE
61c: THROUGH-HOLE
71a: SURFACE
LR: LIGHT RECEIVER
LS: LIGHT SOURCE
PM: AUTOMATED GONIOPHOTOMETER
T: TEST PIECE
Ts: MEASUREMENT SURFACE

The invention claimed is:

1. A metal mask substrate comprising a metal surface to which a resist is to be disposed, wherein a specular reflectance of incident light to the surface is 45.2% or more,
   the metal mask substrate has a width direction orthogonal to a rolling direction of the metal mask substrate,
   a specular reflectance in a first plane orthogonal to the surface and orthogonal to the rolling direction is a first reflectance,
   a specular reflectance in a second plane orthogonal to the surface and orthogonal to the width direction is a second reflectance,
   the second reflectance is larger than the first reflectance, and
   the first reflectance is 45.2% or more.

2. The metal mask substrate according to claim 1, wherein the surface includes a portion in which a difference obtained by subtracting the first reflectance from the second reflectance is 10.2% or more.

3. The metal mask substrate according to claim 1, wherein the surface has a three-dimensional surface roughness Sa of 0.11 μm or less and a three-dimensional surface roughness Sz of 3.17 μm or less.

4. The metal mask substrate according to claim 1, wherein
   the surface is a first surface,
   the resist is a first resist,
   the metal mask substrate further comprising a metal second surface to which a resist is to be disposed, the second surface being a surface opposite to the first surface, and a specular reflectance of incident light to the second surface is 45.2% or more.

5. The metal mask substrate according to claim 1, wherein the surface is made of invar.

6. The metal mask substrate according to claim 1, wherein the resist is a dry film resist, and
the dry film resist is adhered to the surface.

* * * * *